US007445885B2

(12) United States Patent
Heinzle et al.

(10) Patent No.: US 7,445,885 B2
(45) Date of Patent: Nov. 4, 2008

(54) METHOD FOR ANALYZING ENZYME-CATALYZED REACTIONS USING MALDI-TOF MASS SPECTROMETRY

(75) Inventors: Elmar Heinzle, Saarbrücken (DE); Min-Jung Kang, St.Ingbert (DE); Andreas Tholey, Püttlingen (DE); Klaus Hollemeyer, Neunkirchen-Wiebelskirchen (DE); Bernhard Hauer, Fuβgönheim (DE)

(73) Assignee: BASF Aktiengesellschaft (DE)

( * ) Notice: Subject to any disclaimer, the term of this patent is extended or adjusted under 35 U.S.C. 154(b) by 519 days.

(21) Appl. No.: 10/296,381

(22) PCT Filed: Jun. 6, 2001

(86) PCT No.: PCT/EP01/06416

§ 371 (c)(1), (2), (4) Date: Nov. 25, 2002

(87) PCT Pub. No.: WO01/94924

PCT Pub. Date: Dec. 13, 2001

(65) Prior Publication Data

US 2003/0164449 A1 Sep. 4, 2003

(30) Foreign Application Priority Data

Jun. 7, 2000 (DE) ................................ 100 27 794

(51) Int. Cl.
*C12Q 1/00* (2006.01)
*G01T 3/00* (2006.01)
*C25D 5/34* (2006.01)

(52) U.S. Cl. ........................ 435/4; 250/399.07; 205/209

(58) Field of Classification Search ..................... 435/4; 250/399.07; 205/209
See application file for complete search history.

(56) References Cited

U.S. PATENT DOCUMENTS

| | | | | |
|---|---|---|---|---|
| 3,948,731 A | | 4/1976 | Weaver | |
| 5,643,800 A | * | 7/1997 | Tarantino et al. | 436/518 |
| 6,824,982 B1 | * | 11/2004 | Reetz et al. | 435/6 |
| 6,897,072 B1 | * | 5/2005 | Rich et al. | 436/173 |

FOREIGN PATENT DOCUMENTS

WO WO 58504 A1 * 10/2000

OTHER PUBLICATIONS

Whittman et al. "MALDI-TOF MS for Quantification of Substrates and Products in Cultivations of *Corynebacterium glutamicum*" Biotechnol. Bioeng. (Feb. 2001) 76; 642-47.*

Barnes et al. "Liquid Chromatography: Mass Spectroscopy of Isoflavones" J. Medicinal Food (1999) 2(3-4): 111-117.*

Craig et al. "Monitoring protein kinase and phosphatase reactions with matrix-assisted laser desorption/ionization mass spectroscopy and capillary zone phosphopeptide mixtres" Biological Mass Spec. (1994) 23(8): 519-528.*

Suh, et al., Application of capillary electrophoresis to determination of enzyme activity and other properties of phosphatidylinositol-specific phospholipase C, Journal of Chromatography A, 781, (1997), 263-270.

Zenobi, et al., Ion Formation in Maldi Mass Spectrometry, Mass Spectrometry Reviews, (1998), 17, 337-366.

Ens, et al., Properties of Matrix-assisted Laser Desorption. Measurements with a Time-to-Digital Converter, Rapid Communications in Mass Spectrometry, vol. 5, No. 3, (1991). p. 117-123.

Garden, et al., Heterogeneity within MALDI Samples as Revealed by Mass Spectrometric Imaging, Anal. Chem., (2000), 72, 30-36.

Cohen, et al., Influence of Matrix Conditions on the MALDI-MS Analysis of Peptides and Proteins, Anal. Chem, (1996), 31-37. vol. 68.

Strupat, et al., 2,5-Dihydroxybenzoic acid: a new matrix for laser desorption-ionization mass spectrometry, International Journal of Mass Spectrometry and Ion Processes, 111 (1991) 89-102.

Amado, et al., Discrimination Effects and Sensitivity Variations in Matrix-assisted Laser Desorption/Ionization, Rapid Communications in Mass Spectrometry, vol. 11, 1347-1352 (1997).

Gusev, et al., Improvement of Signal Reproducibility and Matrix/Comatrix Effects in MALDI Analysis, Anal. Chem. (1995), 67, 1034-1041.

Hensel, et al., Electrospray Sample Preparation for Improved Quantitation in Matrix-assisted Laser Desorption/Ionization Time-of-flight Mass Spectrometry, Rapid Communications in Mass Spectrometry, vol. 11, 1985-1793 (1997).

Duncan, et al., Quantitative Analysis of Low Molecular Weight Compounds of Biological Interest by Matrix-assisted Laser Desorption Ionization; Rapid Communications in Mass Spectrometry, vol. 7, 1090-1094, (1993).

Goheen, et al., Mass Spectrometry of Low Molecular Mass Solids by Matrix-assisted Laser Desorption/Ionization, Journal of Mass Spectrometry, vol. 32, 820-828 (1997).

Bagree, et al., FEBS Letters, vol. 120, No. 2, (Nov. 1980), pp. 275-277.

* cited by examiner

*Primary Examiner*—Sandra E. Saucier
*Assistant Examiner*—Susan Hanley
(74) *Attorney, Agent, or Firm*—Connolly Bove Lodge & Hutz LLP

(57) ABSTRACT

A process is described for analyzing enzyme-catalyzed conversions of nonpolymeric substrates to nonpolymeric products with the aid of MALDI-TOF mass spectrometry, preferably in the presence of an internal standard on a specific carrier material.

15 Claims, 17 Drawing Sheets

Figure 1a: Phenylmethylamine (= PMA) as internal standard
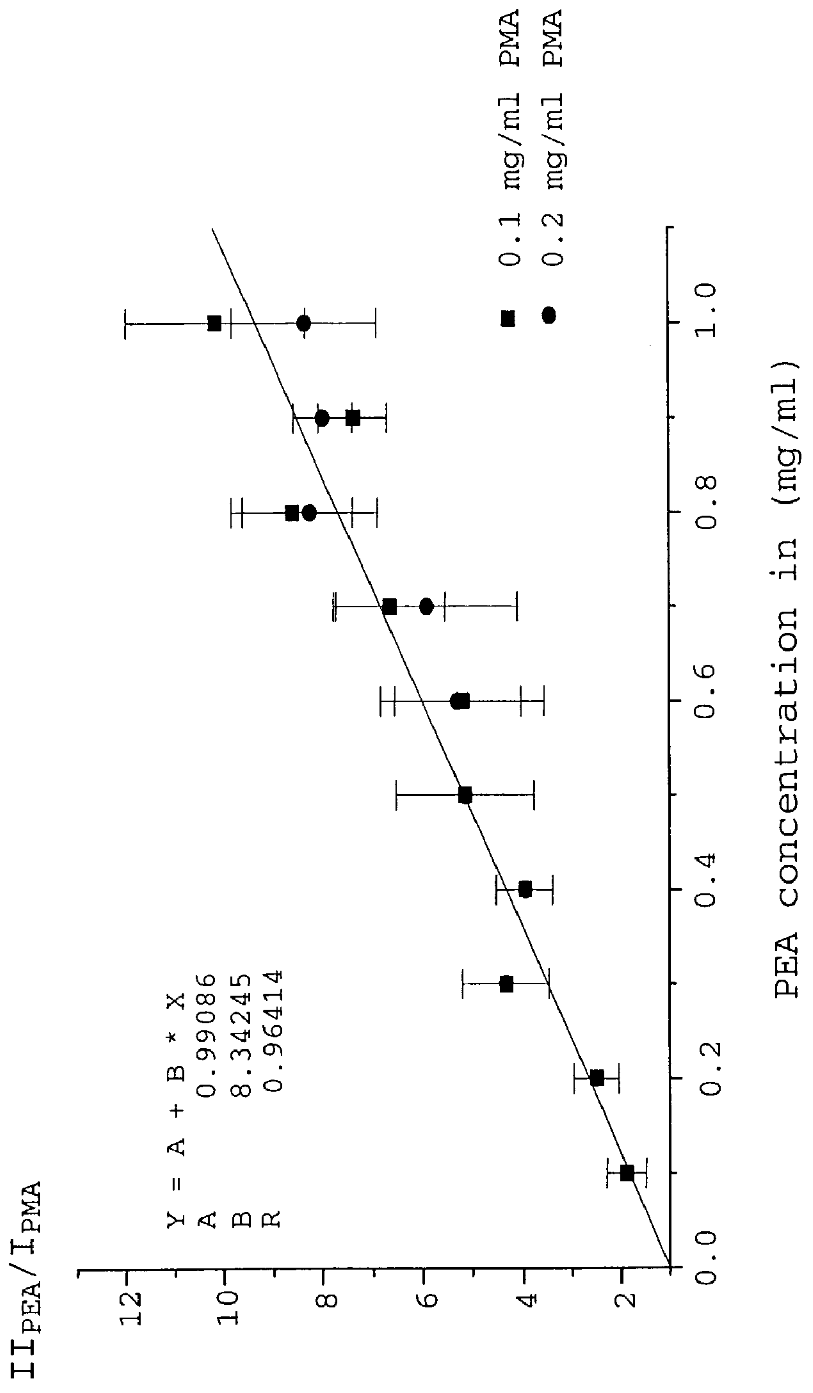

Figure 1b: $d_5$-PEA as internal standard
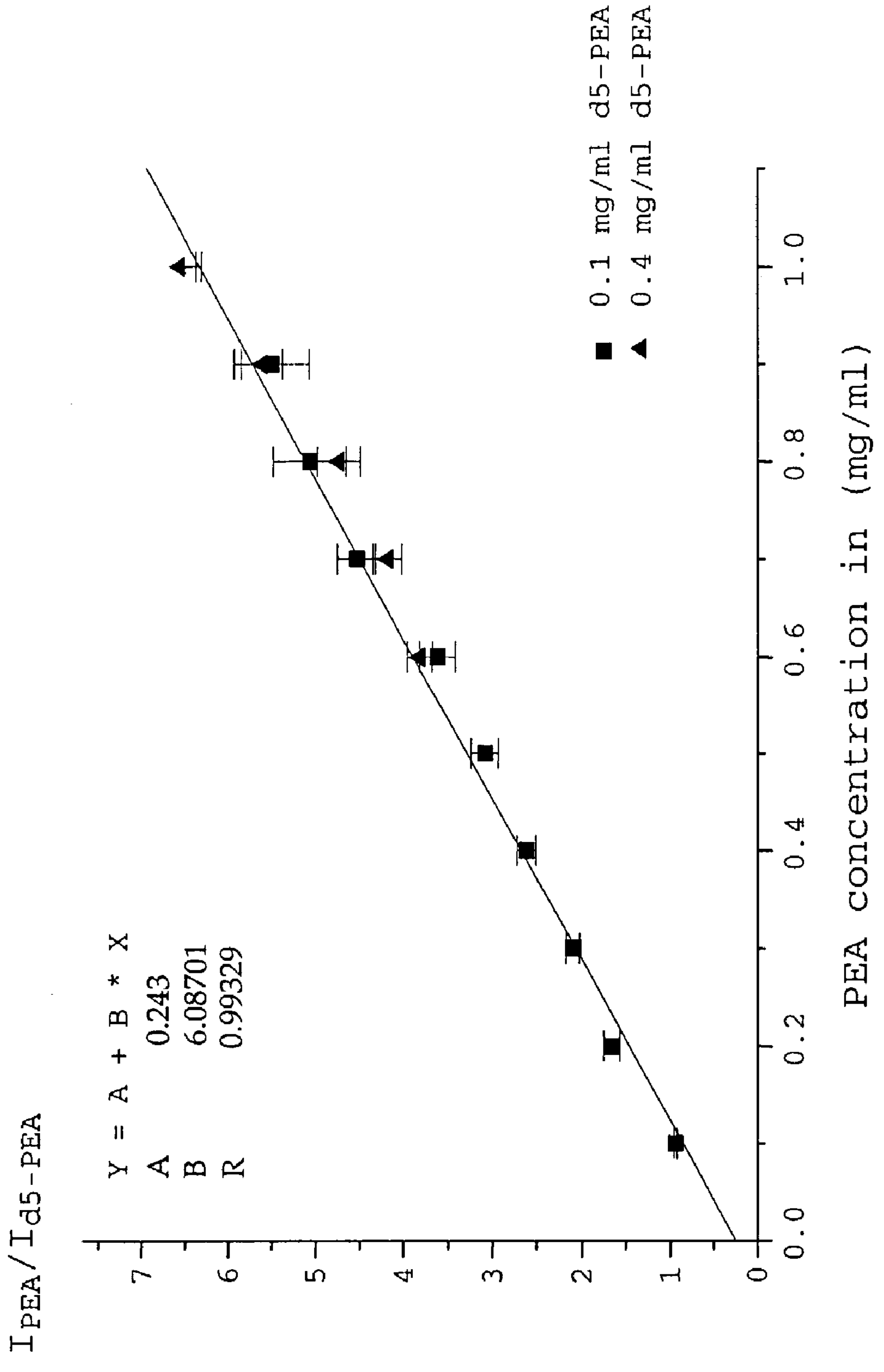

Figure 2: Quantitative determination of PEA against $d_5$-PEA as internal standard
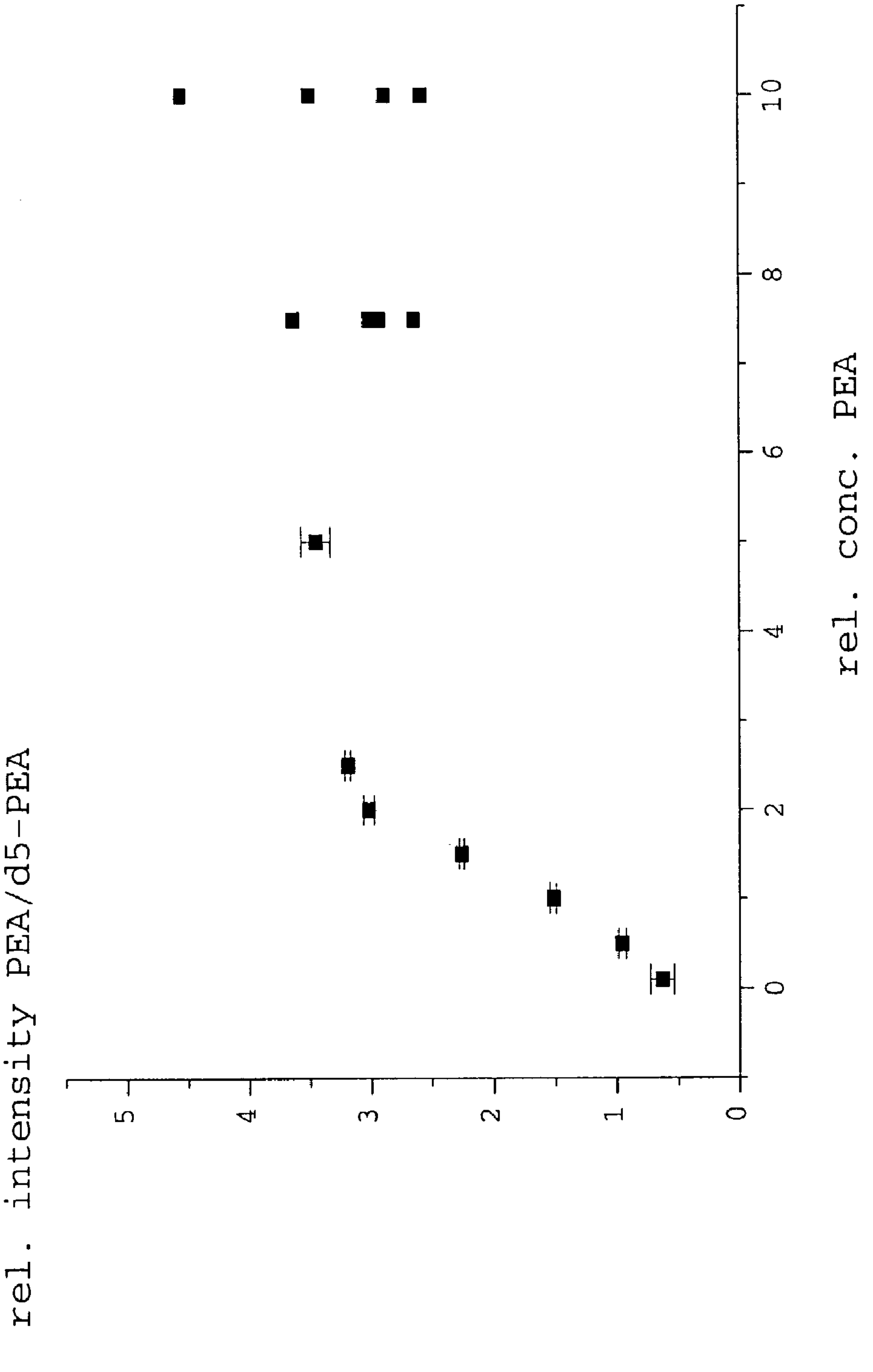

Figure 3: Measurement of PEA against $d_5$-PEA as internal standard in a relative concentration range (A/IS) from 0.1 fold to 2 fold.
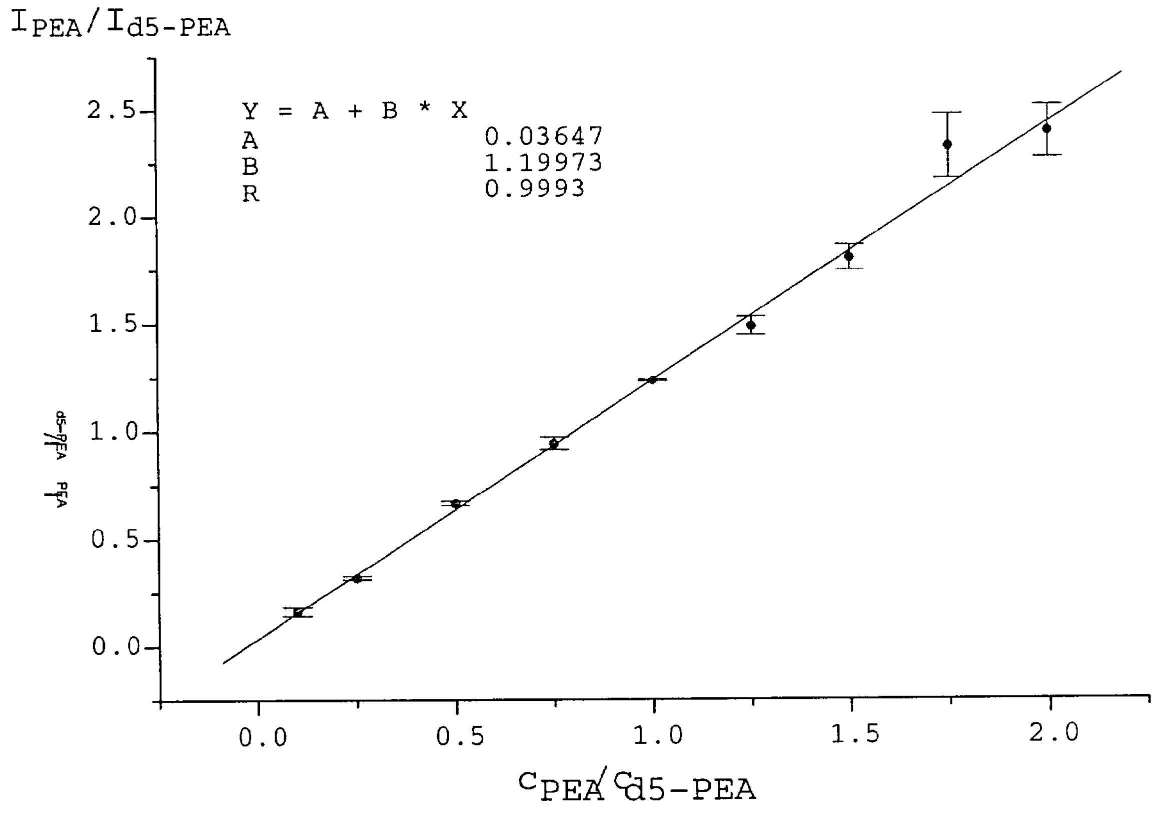

Figure 4: Measurement using the automated program AutoExecute™
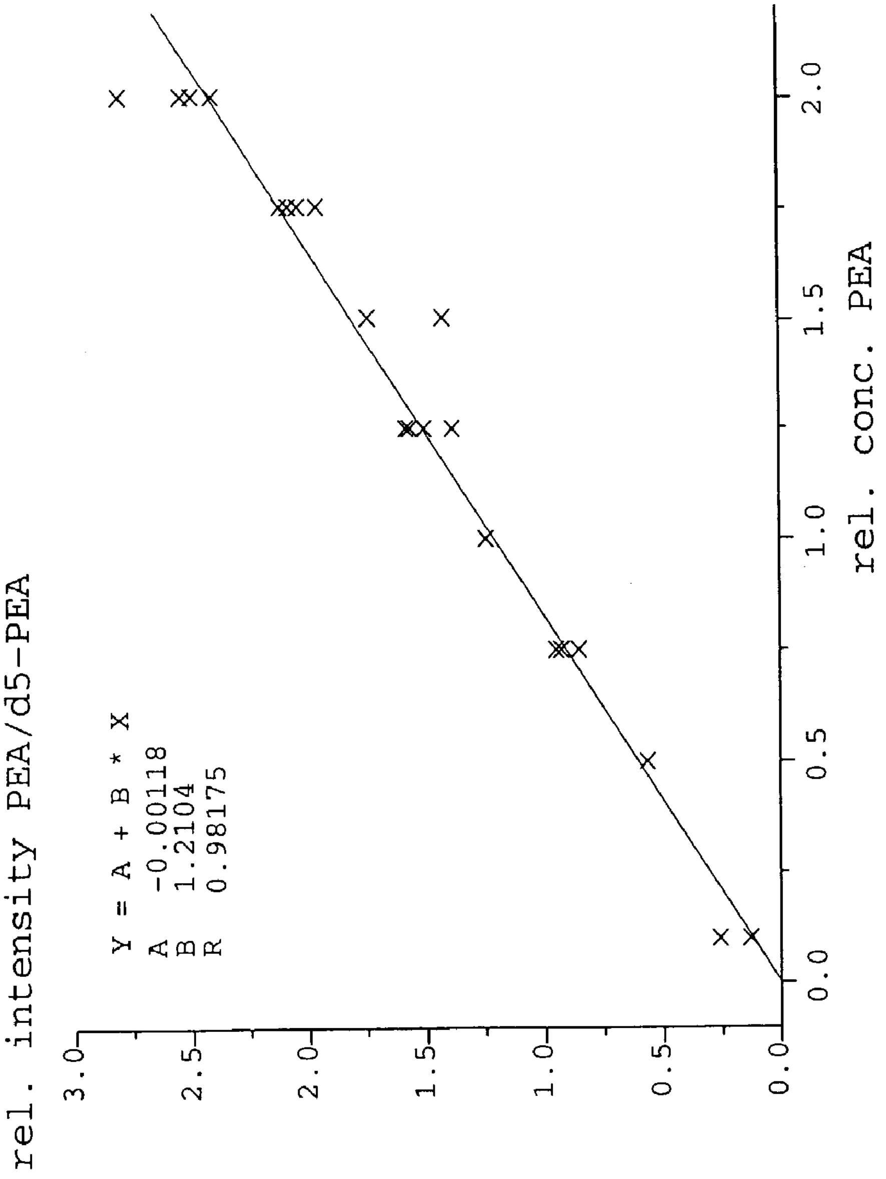

Figure 5a: Profile of A/IS distribution across a sample on the nickel vapor-coated glass target (manual application)
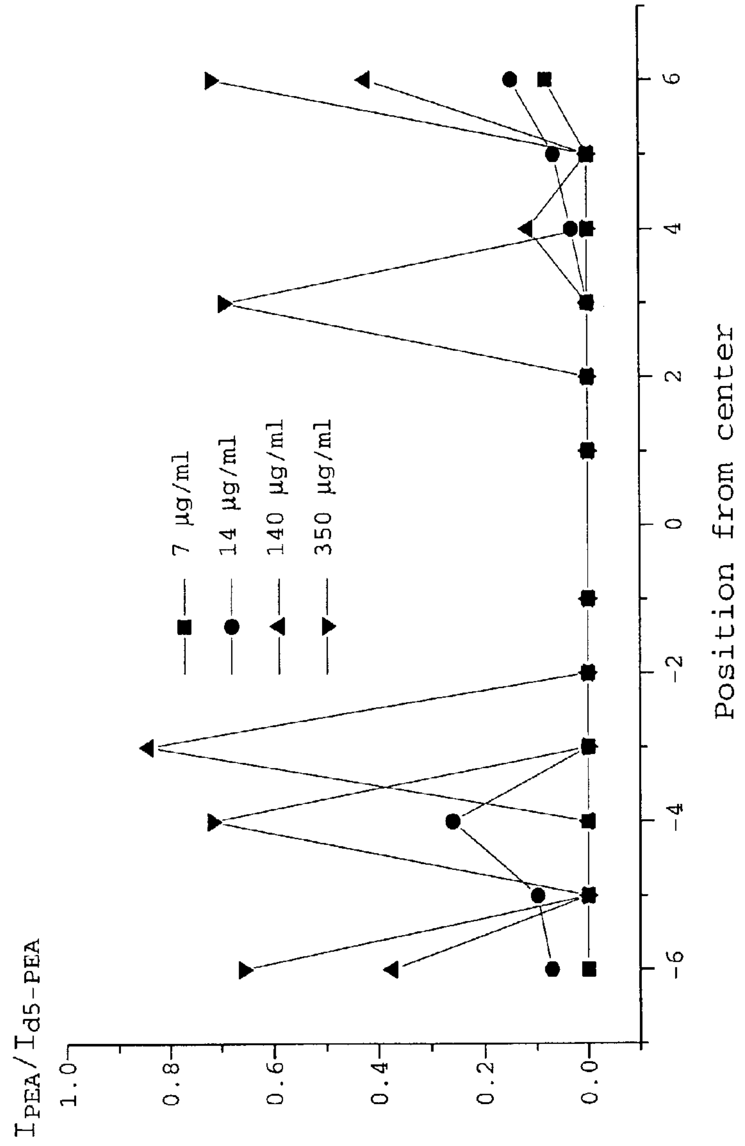

Figure 5b: Profile of A/IS distribution across a sample on the nickel vapor-coated glass target (automatic application)
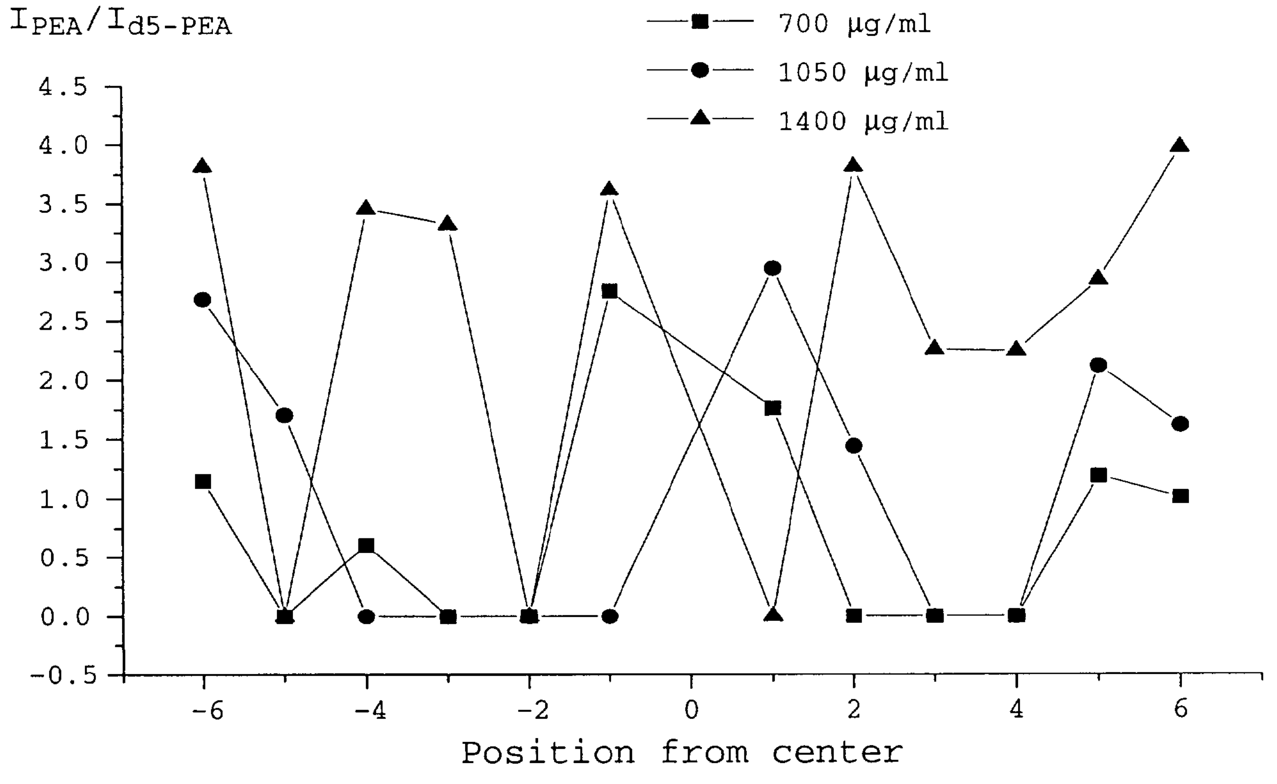

Figure 6a: Profile of A/IS distribution across a sample on the polished metal target (manual application)
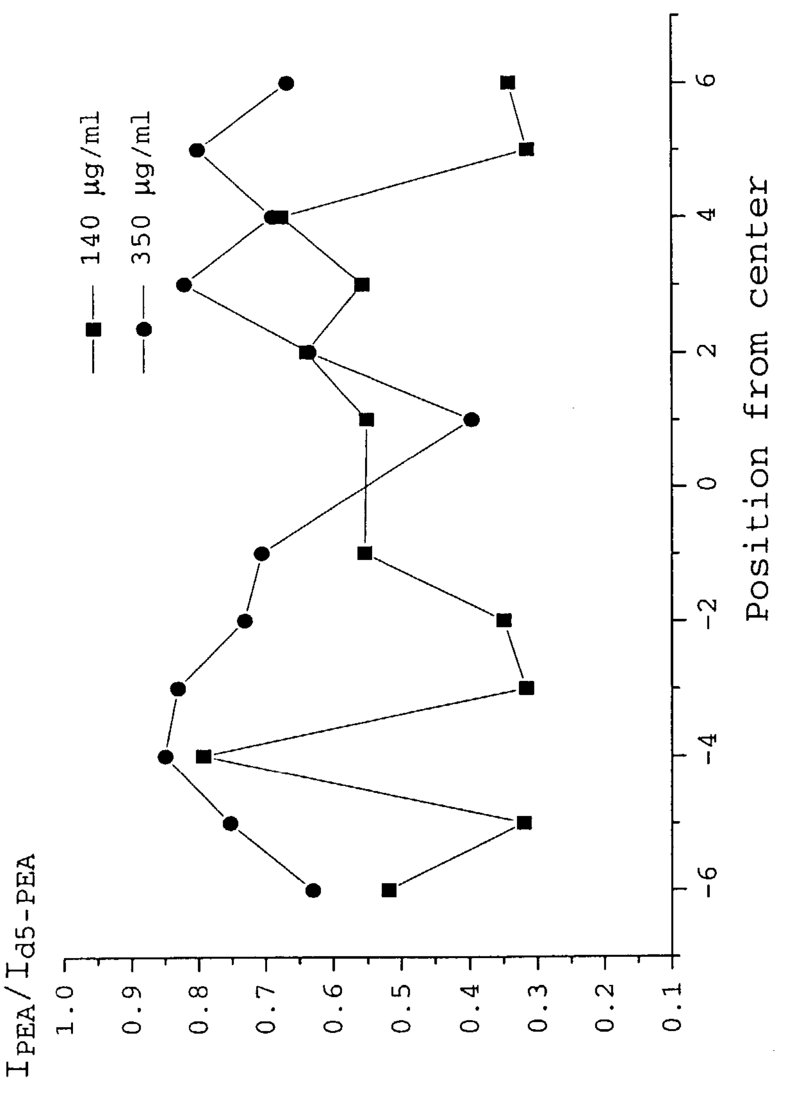

Figure 6b: Profile of A/IS distribution across a sample on the polished metal target (automatic application)
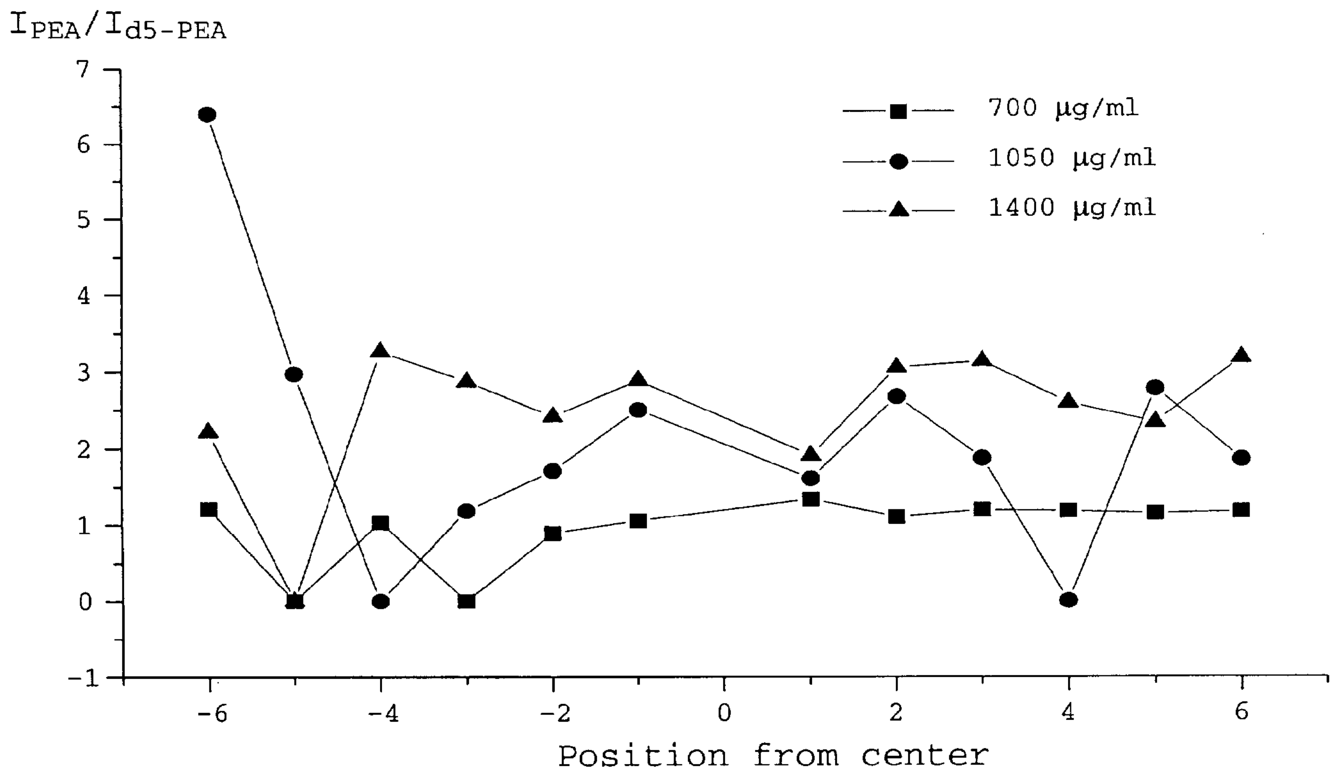

Figure 7a: Quantitative analysis of PEA (7 µg/ml to 1400 µg/ml) against $d_5$-PEA (140 µg/ml) as internal standard on different targets (polished target)
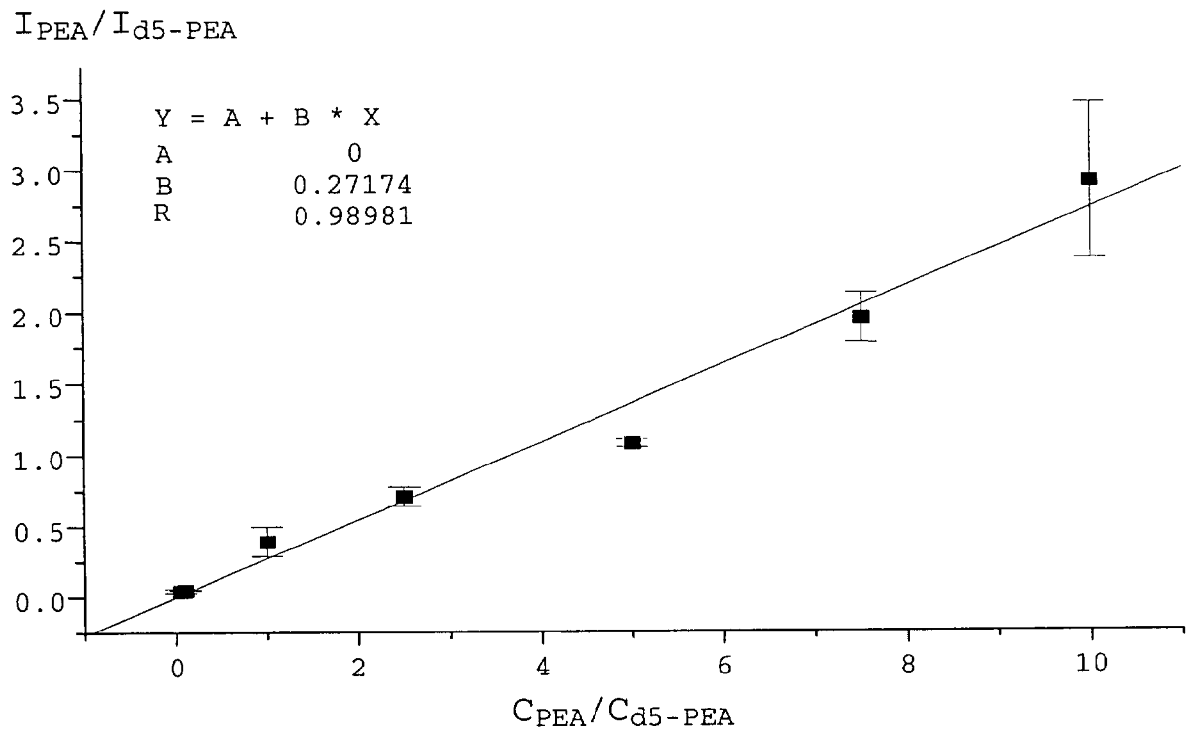

Figure 7b: Quantitative analysis of PEA (7 µg/ml to 1400 µg/ml) against $d_5$-PEA (140 µg/ml) as internal standard on different targets (glass target)
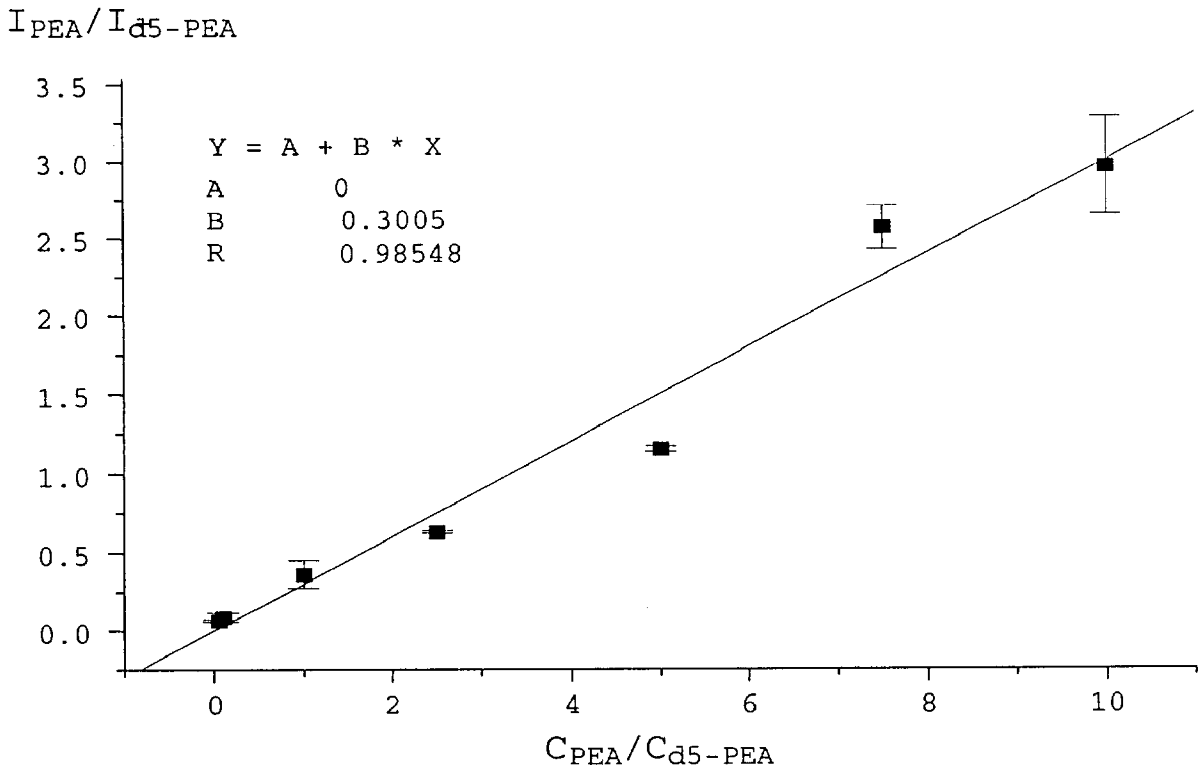

Figure 7c: Quantitative analysis of PEA (7 µg/ml to 1400 µg/ml) against $d_5$-PEA (140 µg/ml) as internal standard on different targets (plate with hydrophilic holes)
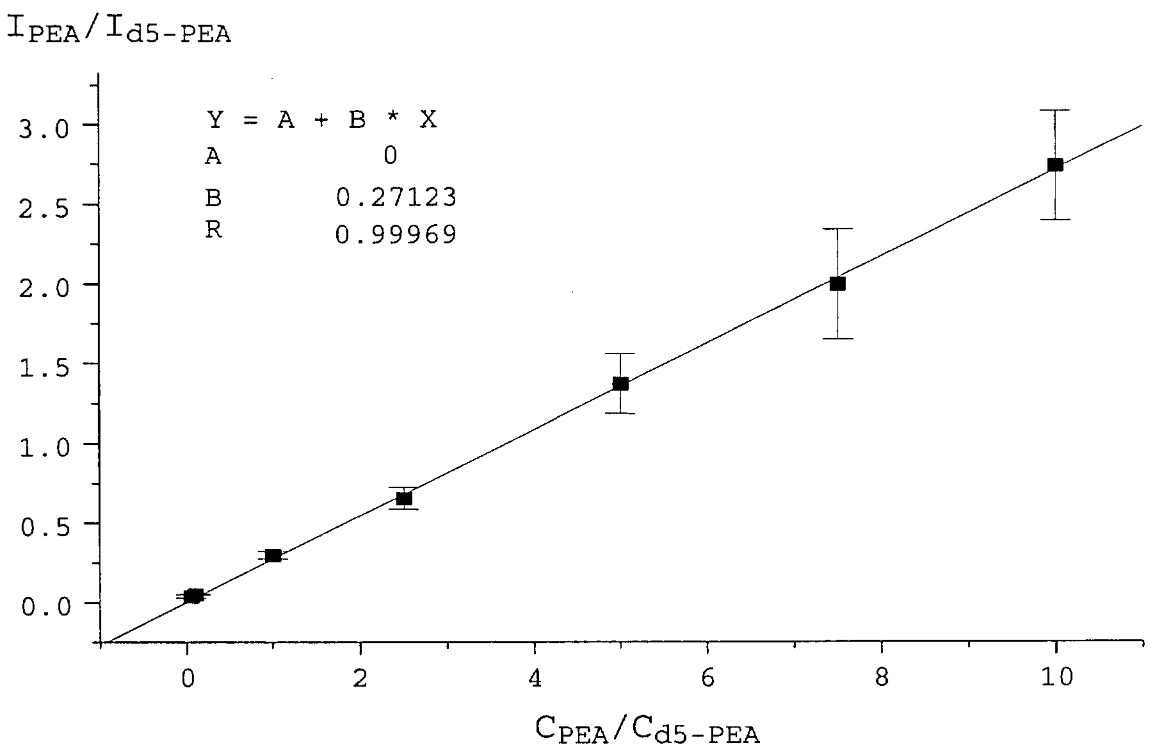

Figure 8: Negative ion MALDI spectrum of unlabeled (MCS, m/z = 313.01) and labeled ($d_3$-MCS, m/z = 316.02) derivatized methoxycyclohexanol. Matrix: ATT.
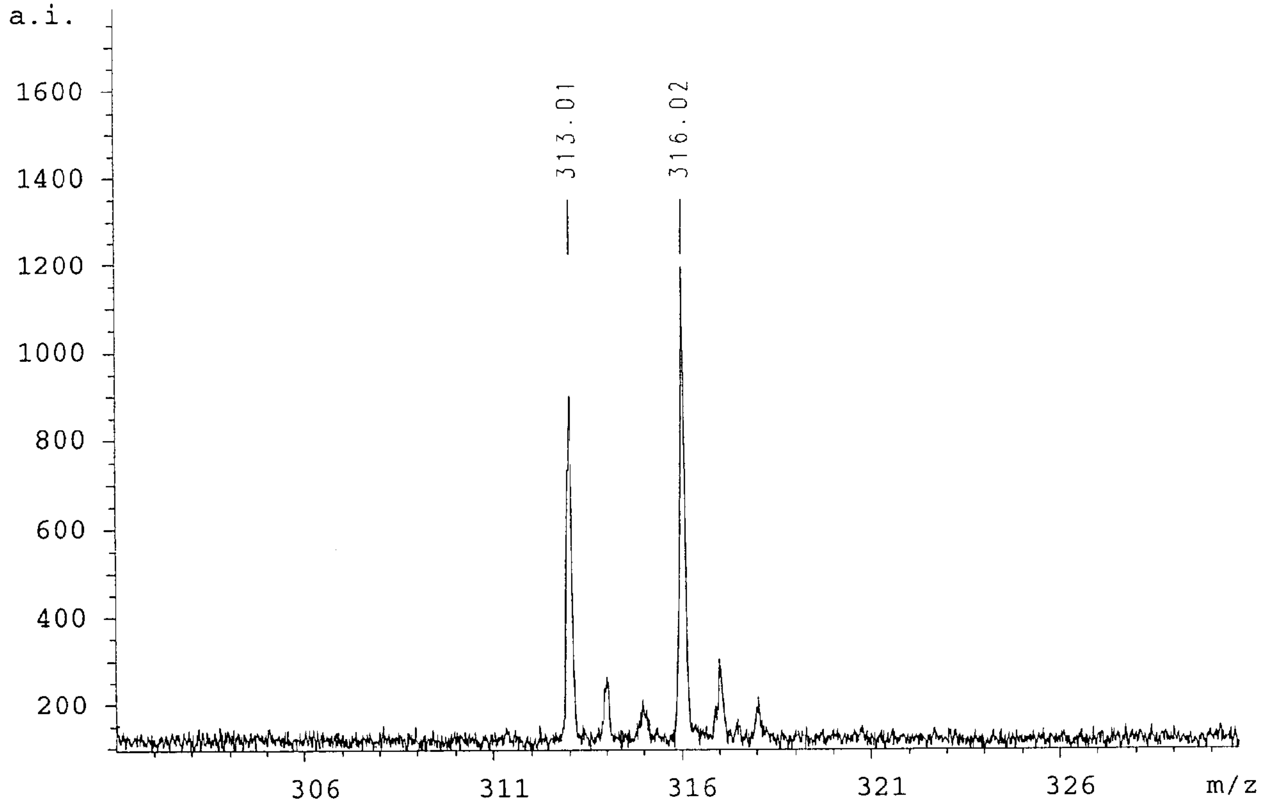

Figure 9: Results of quantitative MALDI of MCS against $d_3$-MCS as internal standard
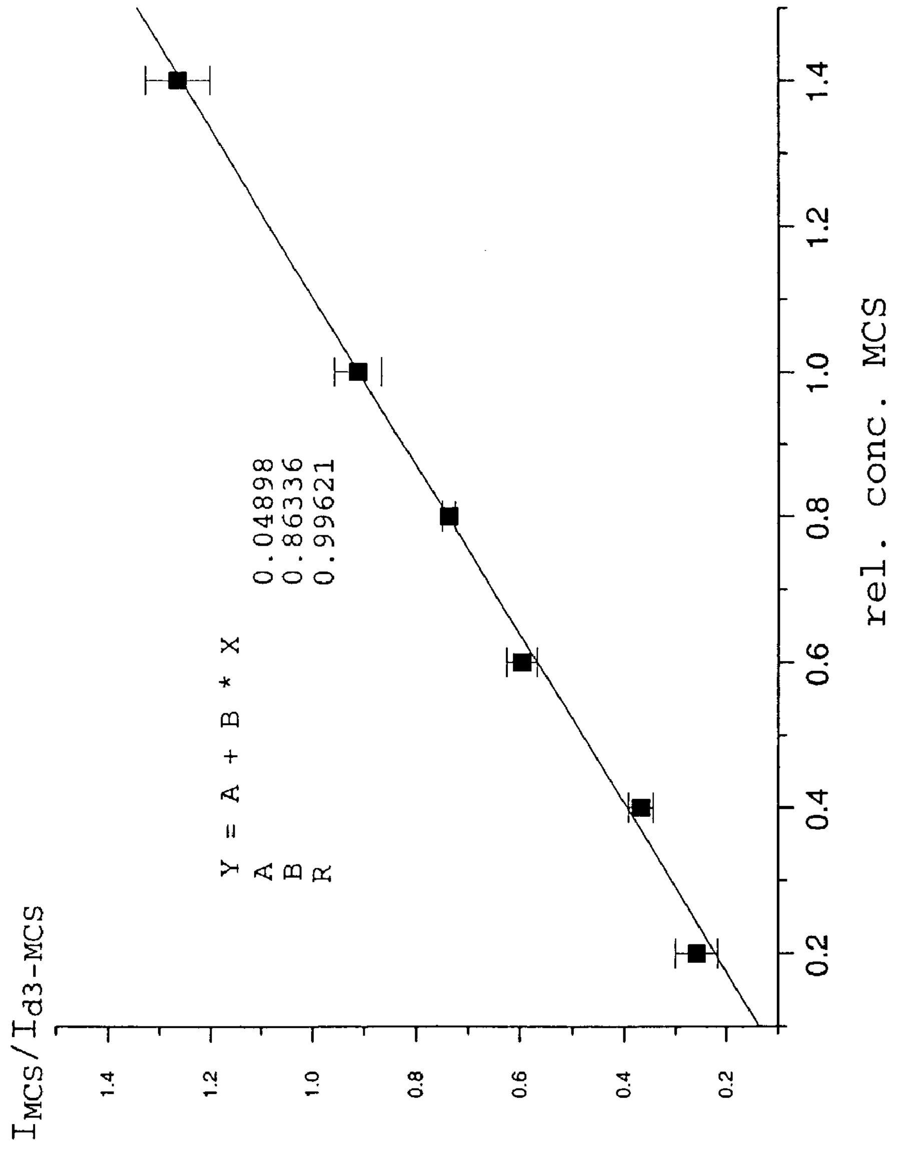

Figure 10: Amount of methoxycyclohexanol (as MCS) before (left) and after (right) conversion using Boehringer lipase. Three different M/A ratios were studied in each case.
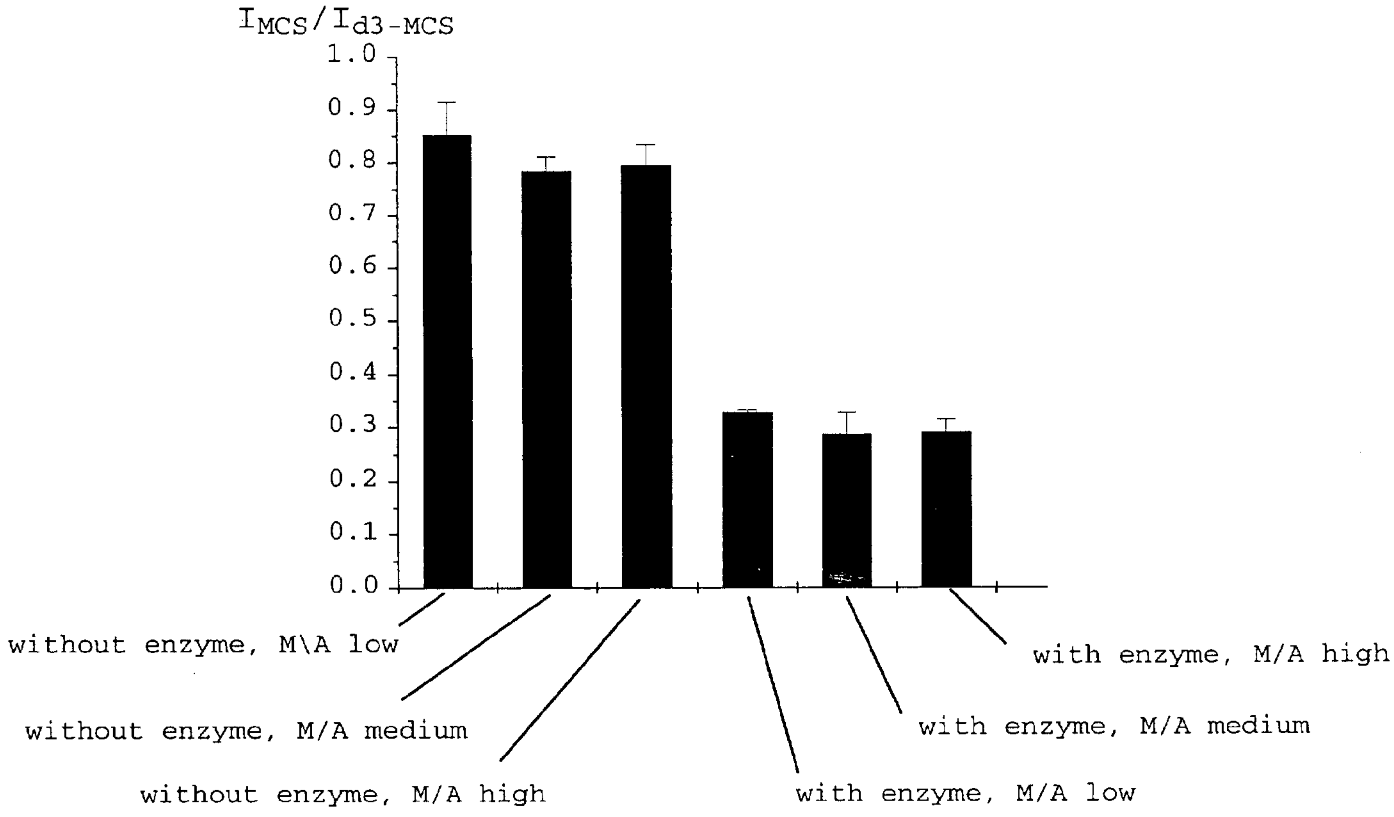

Figure 11: Percentage conversion of enantiomerically pure methoxycyclohexanol, measured at different matrix/analyte ratios.
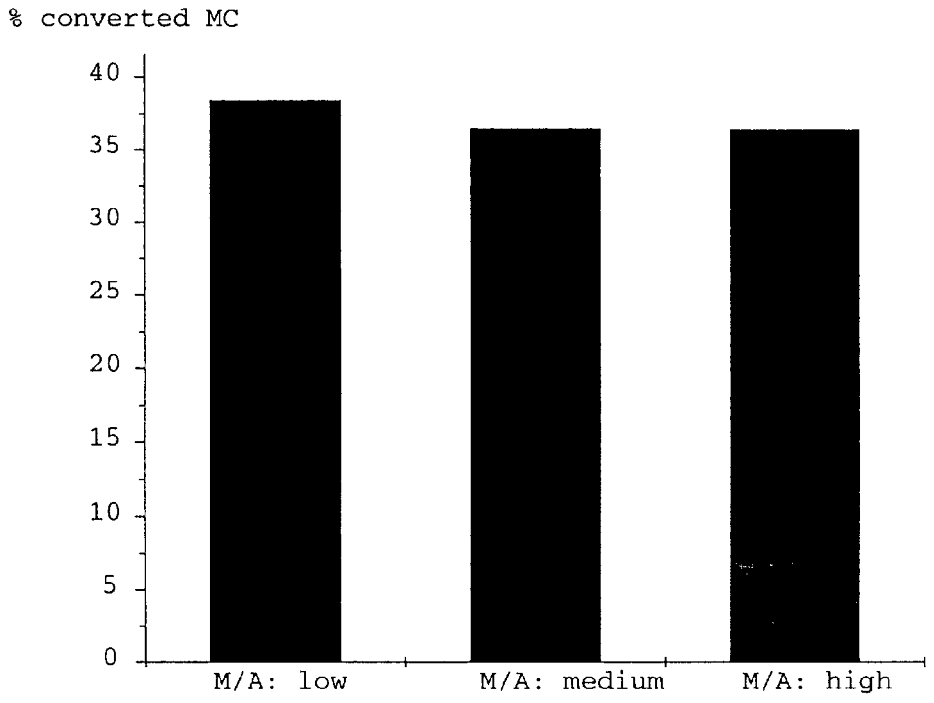

Figure 12: Time course of the enzymatic conversion of racemic methoxycyclohexanol using immobilized lipase
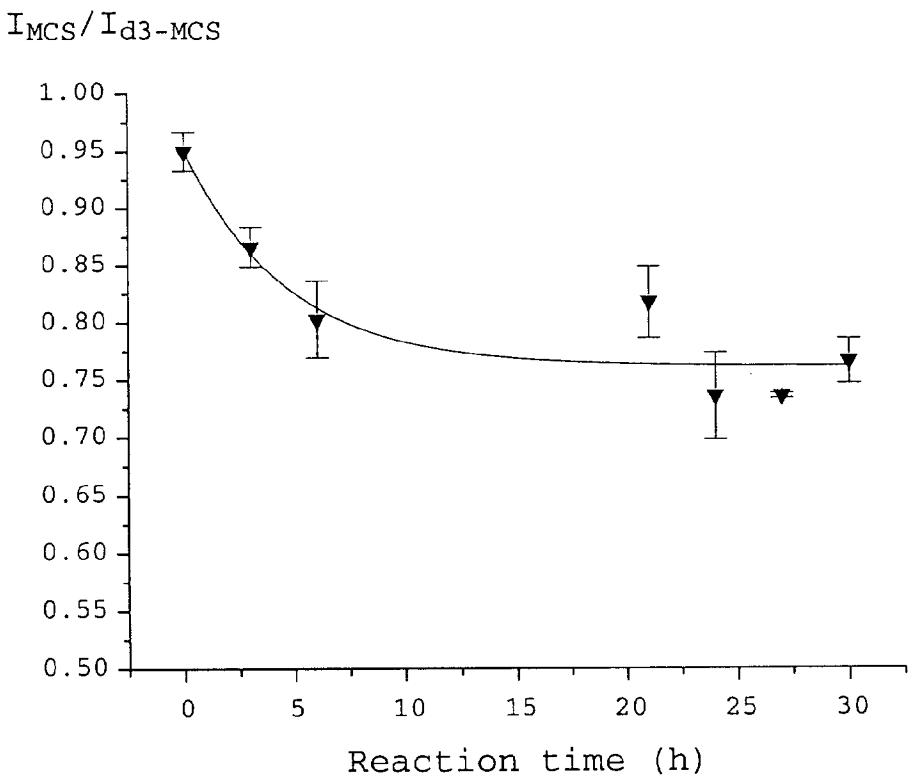

METHOD FOR ANALYZING ENZYME-CATALYZED REACTIONS USING MALDI-TOF MASS SPECTROMETRY

This application is the US national phase of international application PCT/EP01/06416 filed 6 Jun. 2001 which designated the U.S.

The present invention relates to a process for analyzing enzyme-catalyzed conversions of nonpolymeric substrates to nonpolymeric products with the aid of MALDI-TOF mass spectrometry, preferably in the presence of an internal standard on a specific carrier material.

Success in the screening for novel enzymatic reactions depends to a large extent on chance. This kind of screening demands the scrutinizing of a very large number of organisms for the desired enzymatic activity until the desired enzyme activity is found. Screening for these enzyme activities therefore requires rapid, simple, highly sensitive and highly specific analytical processes.

A major problem in the screening for novel enzymatic activities is the quick and simple identification of the products generated in the enzymatic reaction and/or, where appropriate, the decrease in the substrate employed. Product analysis usually involves using separation processes such as thin layer chromatography (=TLC), high pressure liquid chromatography (=HPLC) or gas chromatography (=GC). Processes such as NMR which are usable after work-up via, for example, salt precipitation and/or subsequent chromatography may also be used for analysis. These processes are time-consuming and allow only a limited sample throughput, and therefore those analytical processes are not usable for so-called high throughput screening (=HTS) which involves initial screening for the desired reaction. Advantageously, these methods provide information both about the product and, where appropriate, about the decrease in substrate.

In order to facilitate higher sample throughput in HTS, indirect, readily measurable processes such as color reactions in the visible range, turbidity measurements, fluorescence, conductivity measurements etc. are frequently used. Although said processes are in principle very sensitive, they are also susceptible to faults. Particular disadvantages here are the analysis of a large number of false positive samples in this procedure and, since these are indirect detection processes, the absence of any information about product and/or substrate. In order to be able to exclude these false positives from the further procedure, it is common to use further analytical processes such as, for example, TLC, HPLC or GC after the first screening. This is again very time-consuming.

Generally it can be said that improving the sensitivity and meaningfulness of detection processes regarding the reaction products leads to the slowing down of an assay.

MALDI-TOF MS (=matrix-assisted laser desorption/ionization time-of-flight mass spectrometry) represents a quick and simple process which is used widely for analyzing large non-volatile biomolecules, in particular such as peptides, proteins, oligonucleotides and oligosaccharides or other polymers. High molecular weight materials such as tar, humic acid, fulvic acid or kerogens have also been analyzed by MALDI (Zenobi and Knochenmuss, Mass Spec. Rev., 1998, 17, 337-366).

Quantifying measurement results in MALDI MS is problematic, because the intensity of the signal depends to a high degree on the homogeneity of the applied sample and on the irradiation density of the laser (Ens et al., Rapid Commun. Mass Spectrom, 5, 1991: 117-123), the intensity increasing at first approximation exponentially with increasing laser energy (Ens et al., Rapid Commun. Mass Spectrom, 5, 1991: 117-123). A signal intensity which is too high may possibly lead to signal saturation at the detector, and this also rules out quantification. Besides these problems of physical and technical nature there are other reasons which make a quantitative evaluation of MALDI measurements difficult. Thus, for example, fragments of the ions searched for or molecule adducts may appear. The most serious problem in quantitative MALDI MS, however, is the inhomogeneity of the samples. The quality of a MALDI spectrum is to a great extent dependent on the morphology of the sample studied (Garden & Sweedler, Anal. Chem. 72, 2000: 30-36). As a result, it is possible to observe significant differences regarding the appearance of signals, the intensity, the resolution and the mass accuracy as soon as different sites of a MALDI sample are studied (Cohen & Chait, Anal. Chem., 68, 1996: 31-37; Strupat et al., Int. J. Mass Spectrom. Ion Processes, 111, 1991: 89-102; Amado et al., Rapid Commun. Mass Spectrom., 11, 1997: 1347-1352). These inhomogeneities are based on an uneven distribution of matrix and analyte on the sample target, which is caused by different crystallization behavior of these two components. In order to abolish or minimize these inhomogeneities—which is tantamount to formation of a microcrystalline homogeneous sample topology—a number of suggestions have been worked out previously. These include, for example, the use of comatrices (Gusev et al., Anal. Chem., 67, 1995: 1034-1041), multilayer preparations, the use of solvent mixtures and electrospray preparations (Hensel et al., Rapid Commun. Mass Spectrom., 11, 1997: 1785-1793) (a compilation of these experiments can be found in Garden & Sweedler, Anal. Chem. 72, 2000: 30-6). However, all of these approaches have limitations and are therefore not broadly usable. Quantification therefore continues to be a problem.

In MALDI the samples are usually applied in a thin layer onto a metal surface and then exposed to a pulsed laser. Focusing the emitted ions can increase the resolution in the low mass region of the mass spectra to about 5000 Da.

Duncan et al. (Rapid Communications in Mass Spectrometry, Vol. 7, 1993: 1090-1094) describe analyzing the low molecular weight polar compounds 3,4-dihydroxyphenylalanine, acetylcholine and the peptide Ac-Ser-Ile-Arg-His-Tyr-$NH_2$ with the aid of MALDI and in the presence of internal standards in the form of the corresponding $^{13}C$- and $^{2}H$-labeled compounds and a similar peptide, respectively.

Goheen et al. (J. Mass Spec., Vol. 32, 1997: 820-828) describe the use of MALDI-TOF MS for analyzing the following low molecular weight compounds:

Citric acid, propionic acid, butyric acid, oxalic acid and stearic acid, ethylenediaminetetraacetic acid (=EDTA), N-(2-hydroxyethyl)ethylenediaminetriacetic acid (=HEDTA), ethylenediamine-N,N'-diacetic acid (=EDDA) and nitrilotriacetic acid (=NTA) and sulfate, nitrate, nitrite and phosphate salts. The matrix used in all experiments is 2,5-dihydroxybenzoic acid.

Disadvantageously, both methods are only suitable for measuring pure substances. This problem is addressed by Duncan et al. in their discussion, where they suggest purifying the samples to be measured in order to overcome this difficulty.

Overall however, MALDI-TOF MS is an interesting, simple and quick method which gives specific information about the analyzed substances so that it would be desirable to use MALDI-TOF MS for measuring enzymatic reactions with low molecular weight substances. Its use in high throughput screening would be especially desirable.

It is an object of the present invention to develop a process for analyzing enzyme-catalyzed reactions by using MALDI-TOF mass spectrometry.

BRIEF DESCRIPTION OF THE FIGURES

FIG. 1. PEA determination against internal standards. FIG. 1*a* illustrates PEA concentration with phenylmethylamine as internal standard. FIG. 1*b* PEA concentration with illustrates $d_5$-PEA as internal standard.

FIG. 2 illustrates the quantitative determination of PEA against $d_5$-PEA as internal standard as the ratio of analyte to internal standard.

FIG. 3 depicts the measurement of PEA against $d_5$-PEA as internal standard in a relative concentration range (analyte/internal standard (A/IS)) from 0.1 fold to 2 fold.

FIG. 4 depicts a calibration line using an automated program.

FIG. 5 depicts the profile of the analyte/internal standard (A/IS) distribution across a sample on the nickel vapor-coated glass target. FIG. 5*a* shows the manual application and FIG. 5*b* the automatic application.

FIG. 6 depicts the profile of the A/IS distribution across a sample on thepolished metal target. FIG. 6*a* shows the manual application and FIG. 6*b* the automatic application.

FIG. 7 depicts the quantitative analysis of PEA against $d_5$-PEA as internal standard on different target. FIG. 7*a* shows the polished target, FIG. 7*b* the glass target, and FIG. 7*c* the plate with hydrophilic holes.

FIG. 8 shows a MALDI spectrum of a mixture of unlabeled and labeled derivatized methoxycyclohexanol.

FIG. 9 depicts the results of quantitative MALDI of MCS against $d_3$-MCS as internal standard.

FIG. 10 depicts the amount of methoxycyclohexanol before and after enzymatic conversion.

FIG. 11 depicts the conversion of enantiomerically pure methoxycyclohexanol, measured at different matrix/analyte ratios.

FIG. 12 depicts the time course of the enzymatic conversion of racemic methoxycyclohexanol using immobilized lipase.

DETAILED DESCRIPTION OF THE INVENTION

We have found that this object is achieved by a process for analyzing enzyme-catalyzed conversions of nonpolymeric substrates to nonpolymeric products, which comprises analyzing the substrate and product of the enzyme-catalyzed conversion with the aid of MALDI-TOF mass spectrometry, with said process including the following steps:

a) enzyme-catalyzed conversion of a nonpolymeric substrate to a nonpolymeric product, b) analysis of the substrate or product or of the substrate and product during or after the enzyme-catalyzed conversion (a) using MALDI-TOF mass spectrometry.

Enzyme-catalyzed conversions mean enzymatic reactions involving whole cells which may be of plant, animal, bacterial or fungal origin; yeast cells are also suitable. The enzymatic conversion may be carried out by quiescent, growing, permeabilized or immobilized cells or microorganisms. Enzymes are also suitable for the enzyme-catalyzed conversion. These enzymes may still be included in the permeabilized cells or microorganisms or else be present in crude extracts. For a relatively quick and usually also relatively by-product-free conversion it is possible to use partly purified or purified enzymes, which may be used in free or immobilized form in the conversion. Preferably the reaction is carried out using free, partly purified, purified or immobilized enzymes.

Advantageously, the process of the invention uses enzymes of enzyme classes 1 to 6 (International Union of Biochemistry and Molecular Biology=IUB), preferred are enzyme classes 1 to 4, particularly preferred is enzyme class 3 such as subclasses 3.1 (acting on ester bonds), 3.2 (glycosidases), 3.3 (acting on ether bonds), 3.7 (acting on carbon-carbon bonds) and 3.11 (acting on carbon-phosphorus bonds), very particularly preferred are enzymes such as lipases, esterases or phosphatases such as phytases. Further advantageous enzymes can be found in enzyme class 6.

Nonpolymeric substrates and nonpolymeric products in the process of the invention are compounds which, in particular, are not peptides, proteins, oligonucleotides or polynucleotides or oligosaccharides or polysaccharides or artificial or natural polymers. These nonpolymeric substrates or nonpolymeric products possess a molar mass of less than 1000 Da (=dalton), preferably less than 800 Da, very particularly preferably less than 600 Da.

Besides the analysis of substrate and product of the reaction it is possible and advantageous to follow enzyme reactions with the aid of the process of the invention, i.e. kinetic studies of enzymes can be performed. It is further possible to determine $K_m$, $V_{max}$, enzyme selectivity, reaction yield and the effect of inhibitors on an enzyme reaction. Likewise it is possible to study possible reaction parameters such as temperature or pH with respect to the enzyme-catalyzed reaction.

It is not necessary to purify the reaction solutions of the process of the invention prior to analysis by MALDI-TOF mass spectrometry. The reaction can be measured directly. This is also true for complex sample mixtures. Likewise, it is not necessary to use pure substances for the reaction, although this is certainly possible.

It is advantageous and possible to derivatize prior to the analysis substrates and/or products which are only poorly or not at all detectable in MALDI-TOF MS (see Examples) and to finally analyze them in this form. The derivatization may be carried out before or after the enzymatic reaction. Derivatization is particularly advantageous in those cases where hydrophilic groups, which advantageously carry an additional ionizable function, are introduced into hydrophobic or volatile compounds such as, for example, esters, amides, lactones, aldehydes, ketones, alcohols, etc. Examples of such derivatizations are conversions of aldehydes or ketones to oximes, hydrazones or derivatives thereof or of alcohols to esters, for example with symmetrical or mixed anhydrides. This significantly extends the detection spectrum of the process. Derivatization after the enzymatic conversion makes it possible to directly measure the original substrate of the enzymatic reaction. By using MALDI-TOF MS it is thus possible to analyze even substances containing no chromophore. Compared with other processes, this is a substantial advantage since conventional detection processes, for example, usually have to use artificial substrates, which contain e.g. a chromophore, for visual detection, for example. When optimized for this reaction, said substrates will probably not improve the desired natural enzymatic conversion since optimizing this artificial reaction does not reflect the natural conditions.

In the process of the invention for analyzing enzyme-catalyzed reactions an internal standard is advantageously added. This internal standard makes it advantageously possible to quantify low molecular weight compounds in the reaction solution. This standard may be added to the enzyme-catalyzed conversion before, during or after the enzymatic reaction. In this way, substrate and product or, where appropriate, other intermediates of the reaction may be analyzed and, in the end, quantified. In the end, the intermediates can also be seen as products of the substrate employed at the beginning of the reaction. Using the process of the invention, it is therefore also possible to follow or analyze enzyme reactions which catalyze successive reactions. These may be catalyzed by one enzyme or a plurality of enzymes. By-products may also be analyzed.

The internal standards used are advantageously labeled substances, but chemical compounds similar to the substrates and/or products are in principle also suitable as internal standards. Such similar chemical compounds are, for example, compounds of a homologous series whose members only differ by, for example, an additional methylene group. It is preferred to use substrate or product, which is labeled by at least one isotope selected from the group comprising $^{2}$H, 13C, $^{15}$N, $^{17}$O, $^{18}$O, $^{33}$S, $^{34}$S, $^{36}$S, $^{35}$Cl, $^{37}$C, $^{29}$Si, $^{30}$Si, $^{74}$Se or mixtures thereof, or another labeled chemical compound as internal standard. Advantageously, the substrate is labeled by at least one isotope selected from the group comprising $^{2}$H, 13C, $^{15}$N, 170, $^{18}$O, $^{33}$S, $^{34}$S, $^{36}$S, $^{35}$Cl, $^{37}$Cl, $^{29}$Si, $^{30}$Si, $^{74}$Se or mixtures thereof. For expense and availability reasons the use of $^{2}$H or 13C as isotope is preferred. It is not necessary for these internal standards to be completely, i.e. fully labeled for the analysis. Partial labeling is entirely sufficient. It is advantageous and sufficient to have labels at a distance of from 3 or more dalton to 10 or less dalton. However, measurement is in principle also possible at below 3 dalton or above 10 dalton, but short distances may possibly lead to overlapping with the isotopes of the analyte and longer distances may possibly lead to isotope effects. This makes measurements more difficult but not impossible. It is advantageous, even in the case of a labeled internal standard, to select a substance which has maximum homology, i.e. structural similarity, with the chemical compound to be measured. The greater the structural similarity, the better are the measurement results and the more accurately ca the compound be quantified.

For the process of the invention and particularly for quantifying the substrates, products, intermediates or by-products present in the reaction, it is advantageous to use the internal standard in a favorable ratio to the substrate, product, intermediate or by-product to be measured. Ratios between analyte (=compound to be measured) and internal standard of greater than 1:15 do not improve the measurement results, they are, however, possible in principle. Advantageously, the ratio between analyte and internal standard is adjusted in a range of 0.1 to 15, preferably in a range of 0.5 to 10, particularly preferably in a range of 1 to 5.

It is advantageous to concentrate the analytical samples on a minimum space or on a minimum diameter in order to achieve further improvement in data point resolution and/or measurement accuracy.

The reaction samples in the process of the invention may be prepared either manually or, advantageously, automatically by conventional laboratory robots. Analysis by MALDI-TOF MS may likewise be carried out manually or, advantageously, automatically. Automation of the process of the invention makes it possible and advantageous to use MALDI mass spectrometry for the fast screening of enzyme-catalyzed reactions in high throughput screening. MALDI-TOF MS stands out here due to high sensitivity combined with minimum sample consumption. This method makes it possible to quickly find novel enzyme activities and novel mutants of known enzymes after mutagenesis, for example after conventional mutagenesis using chemical agents such as NTG, radiation such as UV or X-ray radiation, or after site-directed mutagenesis, PCR mutagenesis or gene shuffling.

It is advantageous to use for the process of the invention carrier materials having a value or number of roughness $R_z$ of greater than 1, preferably greater than 2, particularly preferably greater than 3 and very particularly preferably greater than 4. $R_z$ is the averaged peak-to-valley height (μm) which is the arithmetic mean value of the individual peak-to-valley heights of 5 neighboring individually measured sections. The peak-to-valley height is determined according to DIN 4768. These carrier materials are polished, coated or vapor-coated carrier materials or polished and coated carrier materials or polished and vapor-coated carrier materials. The carriers comprise a material selected from the group comprising glass, ceramics, quartz, metal, stone, plastics, rubber, silicon, germanium or porcelain. The material preferably comprises metal or glass.

To determine other analytical data, it is possible in the process of the invention to additionally carry out the analysis with the aid of metastable fragmentation after ionization or of collision-induced fragmentation. This makes it possible to obtain further mass data which make it easier or possible to identify the substrates, products, by-products or intermediates present.

It is advantageous in the process of the invention to measure the dynamics of the labeling pattern and the substrate and product concentrations. This makes it possible to analyze the kinetics of enzymes. In this way it is possible to determine Km and $V_{max}$ of an enzyme.

The following examples illustrate the invention in more detail:

EXAMPLES

Example 1

Lipase-Catalyzed Conversion of Rac. Phenylethylamine (=PEA) to 2-methoxy-N-[(1R)-1-phenylethyl]acetamide (=MET)

Diagram I:

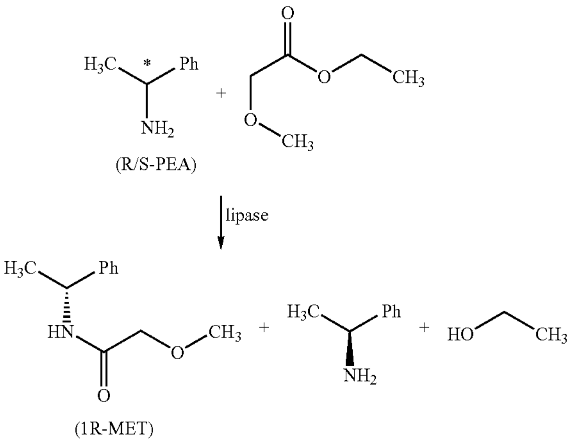

Unless described otherwise in individual examples, the experiments were carried out as follows:

Matrix/analyte ratio=50 (mg/mg)

Solvent: 50% EtOH/50% $H_2O$/1% HOAc/0.1% TFA (v:v:v:v)

Internal standard (IS):$d_5$-PEA $V_{total}$=1 ml

Stock solutions:

DHB: 140 mg/ml

PEA: 35 mg/ml $d_5$-PEA: 35 mg/ml

Pipetting schedule:

| rel. conc. | PEA [mg/ml] | $V_{PEA}$ [µl] | $d_5$-PEA (IS) [mg/ml] | $V_{d5\text{-}PEA}$ [µl] | DHB [mg/ml] | $V_{DHB}$ [µl] | Solvent [µl] |
|---|---|---|---|---|---|---|---|
| 0.1 | 0.014 | 0.4 | 0.14 | 4 | 7.7 | 55 | 940.6 |
| 0.5 | 0.07 | 2 | 0.14 | 4 | 10.5 | 75 | 919 |
| 1 | 0.14 | 4 | 0.14 | 4 | 14 | 100 | 892 |
| 1.5 | 0.21 | 6 | 0.14 | 4 | 17.5 | 125 | 865 |
| 2 | 0.28 | 8 | 0.14 | 4 | 21 | 150 | 838 |
| 2.5 | 0.35 | 10 | 0.14 | 4 | 24.5 | 175 | 811 |
| 3 | 0.42 | 12 | 0.14 | 4 | 28 | 200 | 784 |
| 3.5 | 0.49 | 14 | 0.14 | 4 | 31.5 | 225 | 757 |
| 5 | 0.7 | 20 | 0.14 | 4 | 42 | 300 | 676 |
| 7.5 | 1.05 | 30 | 0.14 | 4 | 59.5 | 425 | 541 |
| 10 | 1.4 | 40 | 0.14 | 4 | 77 | 550 | 406 |

Sample application by nanoplotter

Measurement: manually, 13 positions with 25 shots each

The experimental results are depicted in FIG. 2.

PEA was determined quantitatively in all experiments. It was shown that it is possible to determine MET quantitatively when the internal standard used is PEA; however, in this case the errors were distinctly larger due to the different molecular structures of the two compounds and the different ionization and flight properties associated with said structures. A similar behavior was observed when determining PEA against phenylmethylamine as internal standard (FIG. 1*a*). The best results were obtained with the internal standard having maximum molecular homology, that is structural similarity, to the analyte, as for example $d_5$-PEA to PEA (FIG. 1*b*).

Example 2

Effect of the Ratio of Analyte to Internal Standard on Quantification a) Measurement Over a Relatively Wide Range of Relative Concentrations (0.1 to 10 Fold)

In this experiment the ratio of analyte to standard was varied from 0.1 times to 10 times. The result is shown in FIG. 2. The samples were applied by means of nanoplotter and measured by manually approaching the spots in the MALDI. For each spot 13 positions were measured with 25 shots each and then the results were added up. All concentrations were determined 4 times in each case. The absolute concentration of the internal standard was 0.14 mg/ml.

Samples are prepared according to the abovementioned pipetting schedule (Example 1) and transferred into a 96-well plate.

The nanoplotter is programmed such that for each concentration 50 µl of the sample solution are drawn in; four spots for each concentration are then spotted onto different zones of the MALDI target (quadruple determination).

The exact volume of each spot was not determined, but it is in the order of 0.5 nl.

In order to ensure a reproducible drop formation in the nanoplotter, the parameters for the piezocrystal were varied with the aid of the stroboscope on the nanoplotter and subsequent examination of the spots through a binocular microscope. Typical parameters used in the PEA experiment were:

f=150 Hz (pumping frequency)

T=20 µs (pulse width)

U=60 V (amplitude)

In many cases it was possible to observe the formation of satellite spots which are a well-known phenomenon for this sample application technique but which had no effect on the measurement results. Optimum values vary greatly, depending on concentration ratios!

FIG. 2 depicts the quantitative determination of PEA against $d_5$-PEA as internal standard. A saturation of the curve is clearly visible when the ratio of analyte to internal standard becomes too high.

After a linear increase a distinct saturation of the curve can be seen. The reason for this must be seen in different signal intensities of the two signals at a large concentration difference. At a high analyte/standard ratio (=A/IS) it is thus possible, for example, for the analyte signal to be at the detector limit (256 counts/shot), whereas the signal of the internal standard is just above the required quality criterion of the signal-to-noise ratio.

b) Measurement Over a Narrow Relative Concentration Range

In this experiment, the ratio of analyte to internal standard was varied from 0.1 times to 2 times. The result is shown in FIG. 3 [measurement of PEA against $d_5$-PEA as internal standard in a relative concentration range (A/IS) of 0.1 times to 2 times]. Sample preparation and measurement made use of the same parameters as in the previous experiment (Example 2a). As in Example 2a, there was in the lower range a distinct linear dependence of the signal intensity ratio of A to IS on the relative concentrations of the two components. This range therefore is also advantageous for enzyme assays. Since the starting concentrations are known in an enzyme assay, it is possible readily to calculate the concentration of the internal standard or the ratio of analyte, for example product, to internal standard, in order to obtain a favorable ratio to the analyte. The relative standard deviation in this experiment was usually less than 5%.

Example 3

Sample Application Using a Nanoplotter

Preparing the samples by means of a nanoplotter is intended to apply the minimum amount of the matrix/analyte mixture and to achieve the quickest possible solvent evaporation, which should reduce separation of the two components.

It was possible to show that the nanoplotter permits a simple and rapid preparation of MALDI samples which can lead to reproducible results for quantification. The matrix crystals are distinctly smaller compared with manual preparation. In addition, analyte distribution in the matrix seems to be somewhat more homogeneous than in manual preparation (data not shown). However, this preparation type frequently led to the formation of "fried egg-like" structures, i.e. matrix and analyte form a ring which contains no (or at least distinctly less) ionizable material in its center. The formation of such structures seems to be dependent on matrix/analyte concentrations and the solvent used. It was not possible in this connection to establish general rules; it can be said, however, that this phenomenon is also observable in the manual preparation.

However, it was possible to detect two differences between manual preparation and nano-preparation. Thus, it was possible to show that for manual preparation a slightly larger range in the ratio of analyte to internal standard leads to a linear correlation, whereas for the preparation by means of the nanoplotter the above-described saturation (Example 2, FIG. 2) appears quite early. In contrast to this the relative standard deviation was smaller for the nano-preparation than for manual preparation. Both methods provide comparable and satisfactory results. All examples were carried out both manually and automatically.

Automated Recording of Data

For the automated recording of data the program AutoXecute™ was used which is part of the control software of the Bruker Reflex III MALDI-TOF mass spectrometer, and which permits the automated recording of MALDI spectra. It was possible to optimize the parameters of this software for measuring low molecular weight compounds. In this connection, the following items, inter alia, were considered for the automatic data acquisition: saturation effects of the signals of the matrix, the analyte or the internal standard; saturating the detector limit; laser intensity; peak resolution; signal-to-noise ratio; baseline noise, and adding up the appropriate signals.

The following parameters were used for the automated recording of data:

Laser attenuation: 69-63

Recording format: large spiral

Number of peaks added up: 100

Optimum range of A/IS ratio: 1-5

Resolution≧1400

Signal-to-noise ratio>6

Baseline noise=200 a.i.

FIG. 4 depicts, by way of example, a calibration line which was recorded by means of said parameters. The samples were identical to those measured in Example 2b (FIG. 3). Sample preparation was carried out by means of the nanoplotter; the recording spiral had not been optimized for such small sample drops, and therefore a large number of laser shots missed the samples (for each concentration four spots were measured). Nevertheless, a result was obtained which was analogous to the classical recording technique depicted in FIG. 3; in this classical recording technique the measured spots were approached or sighted manually and shot at 13 different positions by 25 laser shots each. The signals of these 13×25 measurements were added up by the MALDI spectrometer and represent the result of a single measurement. Manual sample preparation gave analogous results. Thus the use of the program AutoXecute™ permits the automated quantification of low molecular weight compounds.

Example 4

Influence of the Target Characteristics

In order to study possible effects of the target characteristics on sample homogeneity, four different MALDI targets were employed:

Unpolished metal target

Polished metal target

Nickel vapor-coated glass target

Hydrophobically coated plate with small holes (the holes for their part have the same characteristics as the unpolished target.)

The experiments were carried out as described in Examples 1 and 2. The unpolished target proved to be unsuitable in both manual preparation and preparation by means of the nanoplotter, since the grooves on the surface caused an inhomogeneous crystallization.

When using the nanoplotter, it was impossible to detect any differences between polished metal target and glass target regarding sample homogeneity and analyte distribution in the matrix, so that in this case using either plate leads to equivalent results in quantification. However, the glass target had the advantage that very small sample spots were more clearly visible in the video microscope of the MALDI apparatus.

Results:

One profile of the analyte/IS ratio across a manually applied spot was plotted for each of the different concentrations (FIGS. 5*a*+5*b*, 6*a*+6*b*). FIG. 5 depicts the profile of the analyte/internal standard (=A/IS) distribution across a sample on the nickel vapor-coated glass target. FIG. 5*a* shows the manual application and FIG. 5*b* the automatic application.

Comparison of FIGS. 5*a*+5*b* with FIGS. 6*a*+6*b* shows that in the case of manual preparation the distribution of analyte and standard on the glass target is not as homogeneous as on the polished target.

It can be seen that the intensity distribution at low analyte/matrix concentrations is uneven and that the highest signal intensity is visible at the edge of the spots ("fried-egg shape"). At higher concentrations, sufficiently strong signals are also detected in the center of the spot. This behavior is analogously seen in the preparation using the nanoplotter.

FIGS. 7*a*) to *c*) indicate that the calibration curves are comparable independently of target composition. FIGS. 7*a*)-*c*) show the quantitative analysis of PEA (7μg/ml to 1400 μg/ml) against $d_5$-PEA (140 μg/ml) as internal standard on different targets. The samples were applied manually (0.34 μl per well). The average standard deviation was about 10% for all three targets. The best data (relative standard deviation≦5%) were obtained, as already described above, for A/IS ratios from 1 to 5. Very good results were obtainable when using the target having small hydrophilic holes ($R^2$=0.9994). Concentrating the sample on a smaller area thus achieves a gain in accuracy.

Example 5

Lipase-Catalyzed Preparation of Enantiomerically Pure 1S,2S-methoxycyclohexanol (MC)

The following reaction which is depicted in diagram II and catalyzed by a lipase was used as a model reaction for a MALDI-TOF MS-based method for quantitative screening of enzymatic reactions.

Diagram II: Lipase-catalyzed preparation of enantiomerically pure 1S, 2S-methoxycyclohexanol (MC)

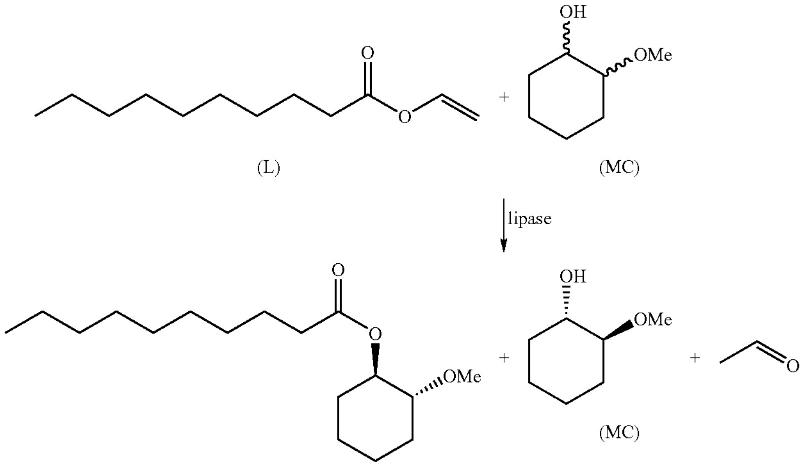

To establish a screening assay using the reaction depicted in diagram II, it was firstly determined whether it is possible at all to detect the molecules involved in the reaction by means of MALDI MS. In addition, a number of different matrices were tested which for their part have acidic or basic properties and should facilitate or improve detection. The compounds studied of the reaction were:

Vinyl decanoate (L)

Methoxycyclohexanol (MC)

Methoxycyclohexanyl decanoate (MCL)

Additionally, it was attempted in one case to induce the formation of sodium adducts by adding NaCl. In the case of two matrices, SDS was additionally added.

In all cases the attempt was made to measure in both positive and negative mode.

Table 1 lists the molar masses and the expected ions (calculated) of the individual compounds.

TABLE 1

Theoretically expected signals

| Compound | Molecular formula | Mono-isotopic molecular weight. | $[M + H]^+$ | $[M + Na]^+$ | $[M - H]^-$ |
|---|---|---|---|---|---|
| Vinyl decanoate (L) | $C_{12}H_{22}O_2$ | 198.162 | 199.169 | 221.152 | 197.154 |
| Methoxy-cyclohexanol (MC) | $C_7H_{14}O_2$ | 130.099 | 131.107 | 153.089 | 129.091 |
| Methoxy-cyclohexanyl decanoate (MCL) | $C_{17}H_{32}O_3$ | 284.235 | 285.243 | 307.225 | 283.227 |

Table 2 lists the different matrices used for carrying out the measurements and the results of these measurements.

TABLE 2

Matrices used and results of measurements in positive and negative modes. +: Signal detected, −: signal not detected, * overlapping of a (theoretical) signal with a matrix signal.

| Compound | L (pos) | L (neg) | MC (pos) | MC (neg) | MCL (pos) | MCL (neg) |
|---|---|---|---|---|---|---|
| 2,5-DHB | — | — | — | — | — | — |
| 2,5-DHB + SDS | — | — | — | — | — | — |
| SA | — | — | — | — | — | — |
| CCA | — | — | — | — | — | — |
| CCA, (M/A) = 1 | — | — | — | — | — | — |
| CCA + SDS | — | — | — | — | — | — |
| CCA + NaCl | — | — | — | — | — | — |
| 2-amino-5-nitropyridine | — | — | — | — | — | — |
| Dithranol/AgTFA | — | — | — | — | — | — |

Abbreviations in Table 2:
2,5-DHB = 2,5-Dihydroxybenzoic acid
SDS = sodium dodecyl sulfate
SA = sinapinic acid
CCA = α-cyano-4-hydroxycinnamic acid Conditions of Measurement:

Measurement in positive and negative mode

All matrix solutions were made up freshly:

CCA, SA, DHB, dithranol/AgTFA: in 90% acetonitrile/10% water/0.1% TFA 2-amino-5-nitropyridine: in 90% acetonitrile/10% water The matrix-to-analyte ratio (M/A) was varied:

M/A=100 (mg/mg)

M/A=30 (mg/mg)

M/A=1 (mg/mg)

Stock solutions of the analytes (in acetonitrile) were prepared.

Evaluation of Results:

Despite varying the conditions (matrices, solvent, pH) it was impossible to detect analyte signals either in positive or negative mode. A possible reason for this is possibly the volatility of the analytes under the MS conditions (high vacuum). Another possible explanation may be the apolar nature of the compounds which makes accessibility of said compounds to MALDI analysis very difficult. In order to be able to follow the reaction, the methoxycyclohexanol was therefore derivatized. For measurement in MALDI MS, methoxycyclohexanol (=MC) was derivatized to give the corresponding methoxycyclohexanyl sulfobenzoate (MCS).

Derivatization of methoxycyclohexanol had two main purposes. Firstly, the derivative should become less volatile and secondly, an ionizable group should be introduced into the molecule. Preliminary experiments using various aromatic acid chlorides (benzoyl chloride, p-nitrobenzoyl chloride) gave unsatisfactory results. The reaction of the alcoholic function with a mixed anhydride (2-sulfobenzoic anhydride (SBA, Bagree et al., FEBS Lett., 120, 1980: 275-277) finally provided the desired success. Diagram III depicts a diagrammatic representation of the derivatization.

Diagram III:

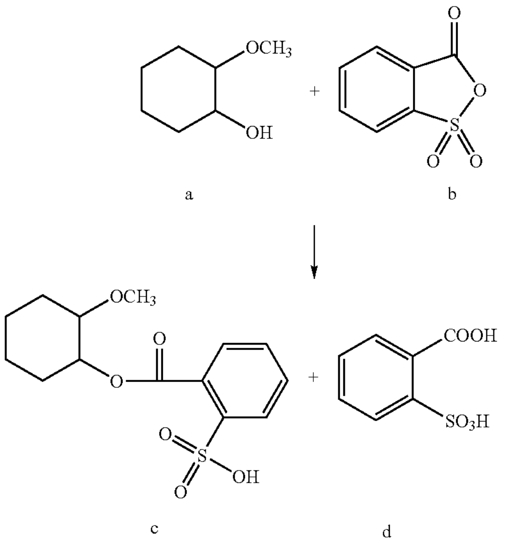

a: analyte: methoxycyclohexanol (BASF)
b: derivatizing reagent: cyclic 2-sulfobenzoic anhydride (Fluka)
c: compound to be measured by MALDI: methoxycyclohexanyl 2-sulfobenzoate (MCS)
d: by-product: 2-sulfobenzoic acid The stereochemistry of methoxycyclohexanol was not taken into account. The model reaction used the following enantiomerically pure compound:

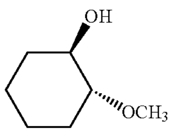

Experimental Procedure

Methoxycyclohexanol (MC)=130.1 g/mol

2-Sulfobenzoic anhydride=184.17 g/mol $d_3$-MC=134.1 g/mol (calculated as $d_4$, since the hydroxyl function is likewise deuterated)

1. Initially charging 0.5 g (3.84 mmol) of methoxycyclohexanol (MC)
2. Dissolving 777.9 mg (1.1 eq., 4,224 mmol) 2-sulfobenzoic anhydride in 0.5 ml acetonitrile (is dissolved completely during the course of the reaction)
3. Adding solution 2) to solution 1)
4. Shaking at room temperature for 2 hours
5. When sample starts crystallizing: dissolving in 2 ml of acetonitrile/1 ml of water (very readily soluble)
6. Preparing MALDI sample Description for Preparing the Standard ($d_3$-MCS): Analogously Weight ($d_3$-MC): 515 mg MALDI Sample Preparation:

a) Theoretically Expected Masses of the Derivative $M_{monoisotopic}$: 314,08
[M+H]+: 315,09
[M+Na]+: 337,07
[M−H]−: 313,07 b) Search for Suitable Matrix

Various matrices were tested which have either acidic or basic properties. Measurements were carried out in negative mode.

TABLE 3

Matrices for measuring the derivatized methoxycyclohexanol (MCS)

| Matrix | pH | Peaks in measured range | evaluation |
|---|---|---|---|
| 2, 5-DHB | acidic | yes | unsuitable |
| SA | acidic | yes | unsuitable |
| CCA | acidic | yes | unsuitable |
| HABA | acidic | yes | unsuitable |
| Trihydroxyacetophenone | acidic | yes | unsuitable |
| 2-Amino-5-nitropyridine | basic | yes | unsuitable |
| ATT (6-aza-2-thiothymine) | basic | 314, 91 | suitable |

The analyte was found in all matrices; the best results and minimum interference from matrix signals, however, were clearly obtained when using ATT.

c) Obtained When Spotting Using the Nanoplotter

The samples were spotted onto the MALDI target by means of a nanoplotter using the conditions of the DHB/PEA solutions used earlier (see pipetting schedule and nanoplotter description, Example 1). Sometimes satellite peaks were detected which had, however, no negative effect on the measurement. The peaks were homogeneous (visual impression from MALDI microscope and binocular).

In the latter measurement no serious variations in the A/IS ratio within the spots were detected (except for the usual variation).

d) Sample Preparation for Quantitative MALDI

Since the true analyte concentration after the reaction (=yield or conversion) was unknown, the various solutions were mixed with each other in different volume ratios.

The matrix solution used was a saturated solution of ATT in AcCN/$H_2O$ (1:1, v:v). A calculation of the accurate matrix/analyte ratio was not possible in this way, but said ratio was kept constant over the entire range measured.

MALDI Measurement:

a) Conditions of Measurement:

negative mode
reflector mode
a polished target was used b) MALDI Spectrum of the Derivatized Methoxycyclohexanol (MCS)

FIG. 8 shows a MALDI spectrum of a mixture of unlabeled (MCS, m/z=331.01) and labeled ($d_3$-MCS, m/z=316.02) derivatized methoxycyclohexanol (matrix: ATT).

Fragments or adducts were not visible under the chosen conditions of measurement. Only the monoisotopic peak was used for subsequent quantitative evaluation, the isotope peaks were neglected.

c) Quantitative Measurement 12 positions per spot were shot at, 25 shots being added up in each case; the sum of 12*25 shots was then evaluated. Four spots were shot at for each concentration. Two outliers were found (at rel. conc. 0.2 and rel. conc. 1.4) which were not taken into account in FIG. 9.

FIG. 9 depicts the results of quantitative MALDI of MCS against $d_3$-MCS as internal standard.

A linear correlation between the ratio of analyte signal intensity to internal standard intensity and the concentrations of the two compounds relative to each other was found. The derivatizing reaction and the MALDI parameters used (matrix etc.) permitted a quantitative evaluation of the reaction. This was confirmed using a commercially available lipase (Boehringer, Mannheim, Germany).

Procedure:

- 1.01 mmol (200 mg) vinyl decanoate and 1.01 mmol methoxycyclohexanol (1.01 mmol) were mixed.
- Enantiomerically-pure MC was used.
- Sample split
  - a) control
  - b) enzyme reaction
- Addition to b) of 50 mg of enzyme. Enzyme: Chirazym L-2, c.-f., C2, Lyo, Boehringer Mannheim; lipase from *Candida antarctica,* fraction B, approx. 4.5 kU/g carrier;
- Addition of 250 µl of hexane to each
- Shaking at room temperature for 24 h
- Solutions were filtered with suction, and subsequently washed with 250 µl of AcCN each
- Addition of 0.5 mmol of $d_3$-methoxycyclohexanol (67 mg, calculated as $d_4$-MC) each
- Addition of 1.5 mmol of 2-sulfobenzoic anhydride (SBA, 276.6 mg) each in 500 µl of AcCN
- Stirring for 20 h
- (Red coloring of the mixtures detected)
- Addition of 27 µl of water (=1.5 mmol) each to stop derivatization
- Mixing of MALDI sample, matrix: saturated ATT, AcCN/water, 1:1
  - a) 20 µl of sample+50 µl of matrix+150 µl of AcCN (M/A: low)
  - b) 20 µl of sample+100 µl of matrix+100 µl of AcCN (M/A: medium)
  - c) 20 µl of sample+200 µl of matrix (M/A: high)
- Applying sample onto target: nanoplotter, polished target
- MALDI measurement, conditions as for model reaction Results:

A distinct reduction in the amount of methoxycyclohexanol after the enzymatic reaction compared with the control reaction was detectable (FIG. 10). It was also possible to demonstrate that the M/A ratio had no great influence on this result. At low M/A ratio the spectra had merely a distinctly lower quality (distinctly poorer signal-to-noise ratio), which can also explain the small deviation from the measurements at medium and high M/A ratios (FIG. 11). FIG. 11 depicts the conversion (in percent) of enantiomerically pure methoxycyclohexanol, measured at different matrix/analyte ratios. The deviation at low M/A ratio is probably due to the poor signal-to-noise ratio for this measurement series.

Example 6

Kinetics of a Lipase-Catalyzed Reaction in Microtiter Plates: Immobilized BASF Lipase The above-specified racemate separation of methoxycyclohexanol was carried out in this experiment in a microtiter plate to which a lipase from *Burkholderia plantarii* had been noncovalently immobilized (BASF, DSMZ 8246).

Experimental Procedure:

- Mixing of 2 g of methoxycyclohexanol and 2.26 g of vinyl decanoate ($V_{total}$=4.275 ml); 200 µl of this solution correspond to 93.5 mg of MC
- 200 µl of this mixture were pipetted into each well of the microtiter plate, the plate was sealed using plate sealer, covered and incubated at room temperature (=28° C.) and 150 rpm on an orbital rotation shaker
- At time t 80 µl were taken from a well (this corresponds to 37.4 mg=2.875*$10^{-4}$ mol of MC). (Furthermore, at the same time 100 µl were transferred into a GC sample vial, overlaid with ethyl acetate (1 ml) and stored at −20° C. until GC analysis).
- To 80 ml of sample 38.6 mg of $d_3$-MC were pipetted (=2.875*$10^{4}$ mol)
- These samples were stored intermediately at −20° C. until completion of the enzymatic reaction so that all derivatization mixtures started at the same time.
- 179 mg of SBA in 400 ml of acetonitrile were pipetted into each of the mixtures which were then shaken at room temperature overnight.
- 20 µl of the derivatization solution were then mixed with 200 µl of saturated ATT solution (water/AcCN, 1:1) in each case and spotted onto the polished metal target by means of the nanoplotter.

Results:

A distinct reduction in the total amount of methoxycyclohexanol was detectable during the course of the enzymatic reaction using immobilized lipase (FIG. 12).

The measurement determined the total amount of MC which was still present after the reaction and which can be both racemic substrate and enantiomerically pure product. The method of the invention made it possible to measure a reduction in the total amount of methoxycyclohexanol by 18% after a reaction time of 30 h.

The results from all experiments make it possible to derive the following:

- Signals should advantageously be recorded at a signal-to-noise ratio of greater than 3; as a quality indicator this ratio advantageously should be greater than 10, which is achievable without problems under the conditions studied.
- Laser attenuation should advantageously be set to a minimum (above threshold), in order to prevent detector saturation and excessive fragmentation of the analyte.
- It is often advantageous to adjust the change in laser attenuation during a series of measurements, in order to prevent saturation of the signal intensities (e.g. rel. conc=0.1, attn: 60/61; rel. conc.=10, attn.: 65/66). This option is also available in the Bruker AutoXecute™ program.

Widening the laser reduces the number of firing positions needed for each spot; it is, however, impossible to cover a drop by one laser position.

Sample homogeneity was greater using the nanoplotter compared with using manual preparation.

The relative errors are below 5% when using the nanoplotter. Optimum results for the lipase reaction are within a narrow concentration range. This means that the analyte concentration ought to be advantageously between 0.1 times and double the concentration of the internal standard.

Due to grooves on the surface, unpolished metal targets are distinctly inferior to polished targets with respect to homogeneous sample preparation and thus unsuitable for quantitative measurement. They are however suitable for qualitative measurement.

Unless stated otherwise in the examples, the experiments were carried out using the following equipment and chemicals:

MALDI Mass Spectrometer:
- Bruker Reflex III MALDI-TOF, Bruker, Bremen, Germany
- $N_2$ laser, $\lambda$=337 nm
- Scout 384-well target
- optionally:
  - polished Bruker standard metal target or
  - Bruker glass target (prototype) or
  - Bruker standard metal target Nanoplotter:
- GeSim micropipetting system nanoplotter, type: P30-x-D Gesellschaft für Silizium-Mikrosysteme mbh, Groβerkmannsdorf/Rossendorf, germany
- piezoelectric micropipette from the same company Chemicals:
- 2,5-DHB: Aldrich
- ATT: Aldrich
- 2-sulfobenzoic anhydride: Fluka
- all other chemicals: BASF (unless stated otherwise)

We claim:

1. A process for analyzing enzyme-catalyzed conversions of nonpolymeric substrates to nonpolymeric products, which comprises analyzing a substrate or a product or a substrate and product of the enzyme-catalyzed conversion with the aid of Matrix-Assisted Laser Desorption/Ionization Time-of-Flight (MALDI-TOF) mass spectrometry, with said process comprising the following steps:

a) enzymatically converting a nonpolymeric substrate to a nonpolymeric product; and b) analyzing the substrate or product or the substrate and product during or after the enzyme-catalyzed conversion of step (a) using MALDI-TOF mass spectrometry, wherein the analysis is carried out on a polished or coated carrier material having a roughness of Rz>I and wherein the substrate or product or the substrate and product are mixed with an internal standard, wherein nonpolymeric substrates and nonpolymeric products are not peptides, proteins, oligonucleotides, polynucleotides, oligosacoharides, polysacoharides, natural polymers or artificial polymers.

2. The process as claimed in claim 1, which comprises adding the internal standard before the start of the enzyme-catalyzed conversion or during or after conclusion of the enzyme-catalyzed conversion and analyzing the substrate or product or substrate and product in the presence of this internal standard.

3. The process as claimed in claim 1, which comprises analyzing substrates or products having a molar mass of <1000 dalton.

4. The process as claimed in claim 1, which comprises quantifying the substrate or product or the substrate and product of the enzyme-catalyzed reaction.

5. The process as claimed in claim 1, which comprises using free or immobilized enzymes, crude extracts or whole cells for the enzyme-catalyzed reaction.

6. The process as claimed in claim 1, wherein the analysis is carried out on a polished and coated carrier material.

7. The process as claimed in claim 1, wherein the carrier material comprises a material selected from the group consisting of glass, quartz, metal, stone, rubber, silicon, germanium and porcelain.

8. The process as claimed in claim 1, which comprises derivatizing the product prior to the analysis.

9. The process as claimed in claim 1, wherein the process is carried out manually or automatically.

10. The process as claimed in claim 1, which comprises using the process in high throughput screening.

11. The process as claimed in claim 1, which comprises using substrate or product, which is labeled by at least one isotope selected from the group consisting of $^{2}H$, $^{13}C$, $^{15}N$, $^{17}O$, $^{18}O$, $^{34}S$, $^{36}S$, $^{35}Cl$, $^{37}Cl$, $^{29}Si$, $^{30}Si$, and $^{74}Se$ or mixtures thereof, or another labeled chemical compound as internal standard.

12. The process as claimed in claim 1, which comprises using substrate labeled by at least one isotope selected from the group consisting of $^{2}H$, $^{13}C$, $^{15}N$, $^{17}O$, $^{18}O$, $^{33}S$, $^{34}S$, $^{36}S$, $^{35}Cl$, $^{37}Cl$, $^{29}Si$, $^{30}Si$, and $^{74}Se$, or mixtures thereof as substrate.

13. The process as claimed in claim 1, wherein the analysis is additionally carried out with the aid of metastable fragmentation after ionization or of collision-induced fragmentation.

14. The process as claimed in claim 1, wherein the coated carrier material is vapor-coated.

15. The process as claimed in claim 6, wherein the coated carrier material is vapor-coated.

* * * * *

UNITED STATES PATENT AND TRADEMARK OFFICE

CERTIFICATE OF CORRECTION

PATENT NO. : 7,445,885 B2 
APPLICATION NO. : 10/296381
DATED : November 4, 2008
INVENTOR(S) : Elmar Heinzle et al.

It is certified that error appears in the above-identified patent and that said Letters Patent is hereby corrected as shown below:

In the Claims:

In Claim 1, in column 17, on line 54, "carrier material having a roughness of $R_Z$>I and wherein" should read -- carrier material having a roughness of $R_Z$>1 and wherein --.

In Claim 1, in column 18, line 5, "nucleotides, oligosacoharides, polysacoharides, natural" should read -- nucleotides, oligosaccharides, polysaccharides, natural --.

In Claim 11, in column 18, on line 38, "$^{17}$O, $^{18}$O, $^{34}$S, $^{36}$S, $^{35}$Cl, $^{37}$CI, $^{29}$Si, $^{30}$Si, and $^{74}$Se or mixtures" should read -- $^{17}$O, $^{18}$O, $^{33}$S, $^{34}$S, $^{36}$S, $^{35}$Cl, $^{37}$Cl, $^{29}$Si, $^{30}$Si, and $^{74}$Se or mixtures --.

Signed and Sealed this

Thirtieth Day of December, 2008

JON W. DUDAS

*Director of the United States Patent and Trademark Office*